United States Patent
Ikeda et al.

(10) Patent No.: US 7,008,376 B2
(45) Date of Patent: Mar. 7, 2006

(54) ELECTRIC BENDING ENDOSCOPE

(75) Inventors: Yuichi Ikeda, Tama (JP); Toshinari Maeda, Hachioji (JP); Haruhiko Ueno, Hachioji (JP); Keiichi Arai, Hachioji (JP); Takayasu Miyagi, Hachioji (JP)

(73) Assignee: Olympus Corporation, Tokyo (JP)

( * ) Notice: Subject to any disclaimer, the term of this patent is extended or adjusted under 35 U.S.C. 154(b) by 95 days.

(21) Appl. No.: 10/673,124

(22) Filed: Sep. 26, 2003

(65) Prior Publication Data

US 2004/0073085 A1    Apr. 15, 2004

(30) Foreign Application Priority Data

Sep. 30, 2002    (JP)    ............................. 2002-287852

(51) Int. Cl.
*A61B 1/00*    (2006.01)

(52) U.S. Cl. ...................................... 600/152; 600/136
(58) Field of Classification Search ................ 600/136, 600/152

See application file for complete search history.

(56) References Cited

U.S. PATENT DOCUMENTS

| | | | | |
|---|---|---|---|---|
| 4,559,928 A | * | 12/1985 | Takayama | 600/152 |
| 4,919,112 A | * | 4/1990 | Siegmund | 600/136 |
| 4,982,725 A | * | 1/1991 | Hibino et al. | 600/117 |
| 5,400,769 A | * | 3/1995 | Tanii et al. | 600/152 |
| 5,658,238 A | * | 8/1997 | Suzuki et al. | 600/150 |

FOREIGN PATENT DOCUMENTS

| | | |
|---|---|---|
| JP | 2-159243 | 6/1990 |
| JP | 4-256724 | 9/1992 |

* cited by examiner

*Primary Examiner*—Beverly M. Flanagan
*Assistant Examiner*—Matthew Kasztejna
(74) *Attorney, Agent, or Firm*—Scully, Scott, Murphy & Presser

(57) ABSTRACT

An electric bending endoscope includes a bending portion arranged to an inserting portion and a bending driving unit which bends the bending portion. In the electric bending endoscope, the bending driving unit includes a motor which generates driving force for bending the bending portion, a first unit which holds the motor, a driving force transmitting member which transmits the driving force of the motor, and a second unit which bends the bending portion by the driving force of the motor. The electric bending endoscope further includes a first holding member which detachably supports, to the first unit, a rotating shaft arranged to the driving force transmitting member of the second unit.

12 Claims, 12 Drawing Sheets

ELECTRIC BENDING ENDOSCOPE

This application claims benefits of Japanese Application No. 2002-287852 filed in Japan on Sep. 30, 2002, the contents of which are incorporated by this reference.

BACKGROUND OF THE INVENTION

1. Field of the Invention

The present invention relates to an electric bending endoscope which electrically bends a bending portion of an inserting portion.

2. Description of the Related Art

Recently, an endoscope is widely used. Various curing treatments are performed by inserting an elongated inserting portion in the celom so as to observe the organ in the celom or by using a treatment tool inserted in a therapeutic instrument channel as needed. In the industrial field, the endoscope observes and examines inner scratches and corrosion of a steam generator, a turbine, an engine and a chemical plant by inserting an elongated inserting portion.

The endoscope has a bending portion which is freely bent on a base end side of an edge portion in the elongated inserting portion. Further, the endoscope receives an instruction as the amount of bending, corresponding to a bending position or a bending speed of the bending portion, by means for inputting a bending operation such as a bending operation lever or a joystick arranged to an operating portion. In the endoscope, a bending operation wire is mechanically stretched or contracted based on the amount of bending inputted as the instruction so as to bend the bending portion.

The above-mentioned endoscope includes an electric bending endoscope in views of the operability. For example, Japanese Unexamined Patent Application Publication No. 2-159243 discloses one of the above-mentioned electric bending endoscopes, in which a built-in motor as bending driving means is controlled for rotation, the motor's driving force enables a bending operation wire to stretch or contract, and the bending portion is electrically bent.

In the electric bending endoscope disclosed in Japanese Unexamined Patent Application Publication No. 2-159243, a bending operation device unit is integrally formed by connecting, to a main frame as a main frame member and a subframe, the motor as the bending operation means, a sprocket as a rotator for the stretch operation which transmits the motor's driving force to the bending operation wire, and the entire bending and stretch mechanism forming portions such as a transmission gear train. Further, the bending operation device unit is enclosed in the operating portion.

Similarly to the electric bending endoscope disclosed in Japanese Unexamined Patent Application Publication No. 2-159243, Japanese Unexamined Patent Application Publication No. 4-256724 discloses an electric bending endoscope in which a bending operation device unit is integrally formed by connecting, to a main frame and the like, a bending and stretch mechanism forming portions and the bending operation device unit is enclosed in the operating portion. The electric bending endoscope disclosed in Japanese Unexamined Patent Application Publication No. 4-256724 accomplishes an object of the present invention to provide the electric bending endoscope which can accurately sets a locking state and a free state with the compact size, light weight, and simple structure.

SUMMARY OF THE INVENTION

Briefly, according to the present invention, an electric bending endoscope comprises: a bending portion arranged to an inserting portion; and a bending driving unit which bends the bending portion. In the electric bending endoscope, the bending driving unit comprises: a motor which generates driving force for bending the bending portion; a first unit which holds the motor; a driving force transmitting member which transmits the driving force of the motor; and a second unit which bends the bending portion by the driving force of the motor. The electric bending endoscope further comprises: a first holding member which detachably supports, to the first unit, a rotating shaft arranged to the driving force transmitting member of the second unit.

The objects and advantages of the present invention will become apparent from the following detailed explanation.

DETAILED DESCRIPTION OF THE PREFERRED EMBODIMENTS

Hereinbelow, a description is given of embodiments of the present invention with reference to the drawings.

(First Embodiment)

Figure 1:
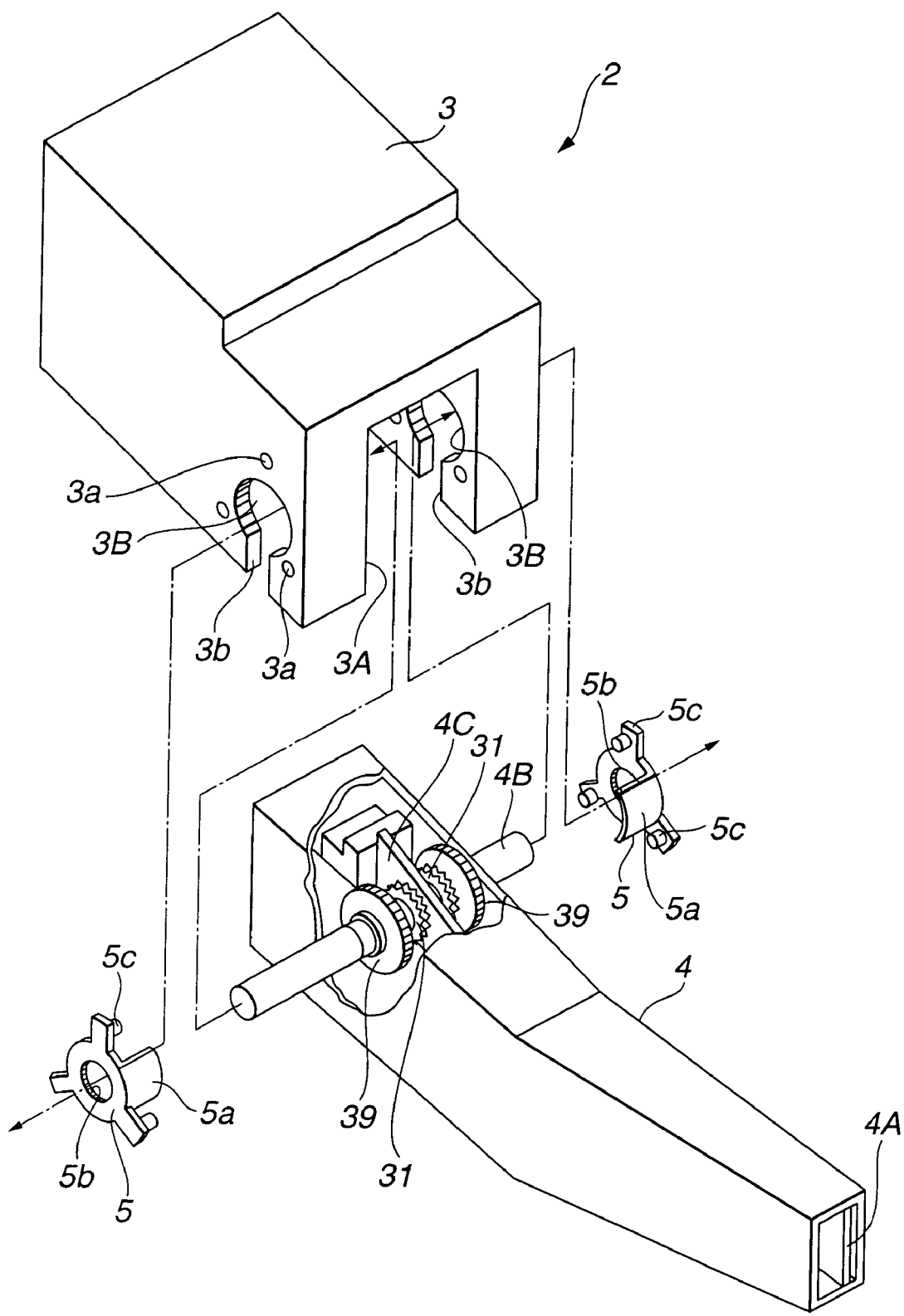
FIG. 1 is an exploded perspective view showing the schematic structure of an electric bending endoscope according to a first embodiment of the present invention.
Figure 2:
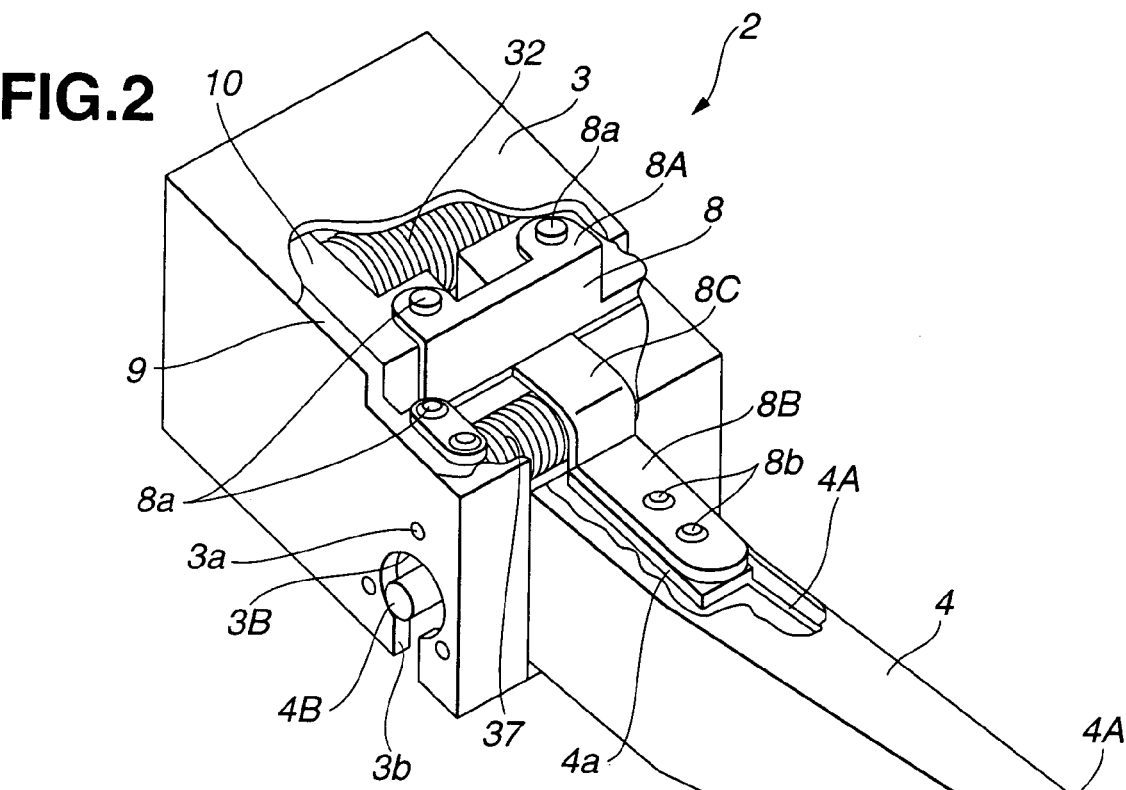
FIG. 2 is a perspective view schematically showing the electric bending endoscope shown in FIG. 1 after assembling, including a cut-off part.
Figure 3:
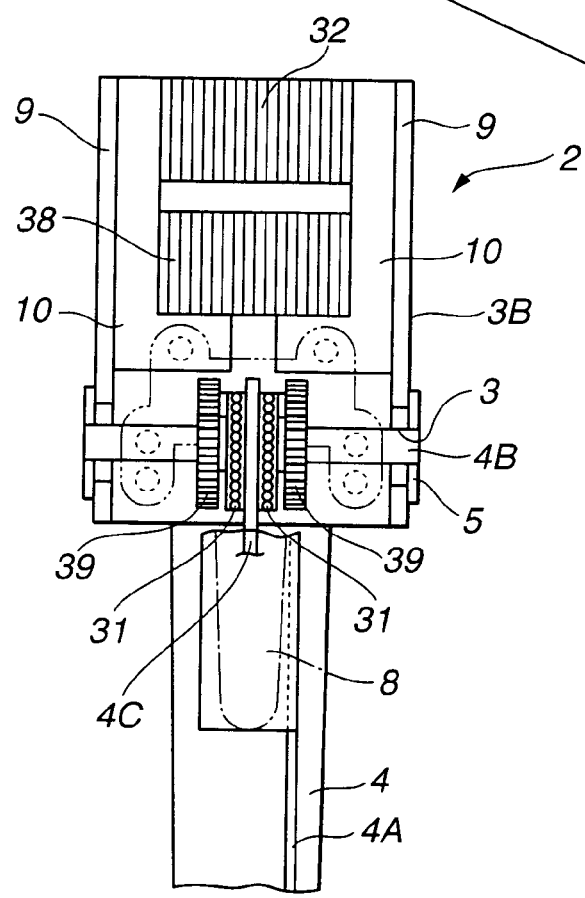
FIG. 3 is a plan view showing the electric bending endoscope shown in FIG. 2.
Figure 4:
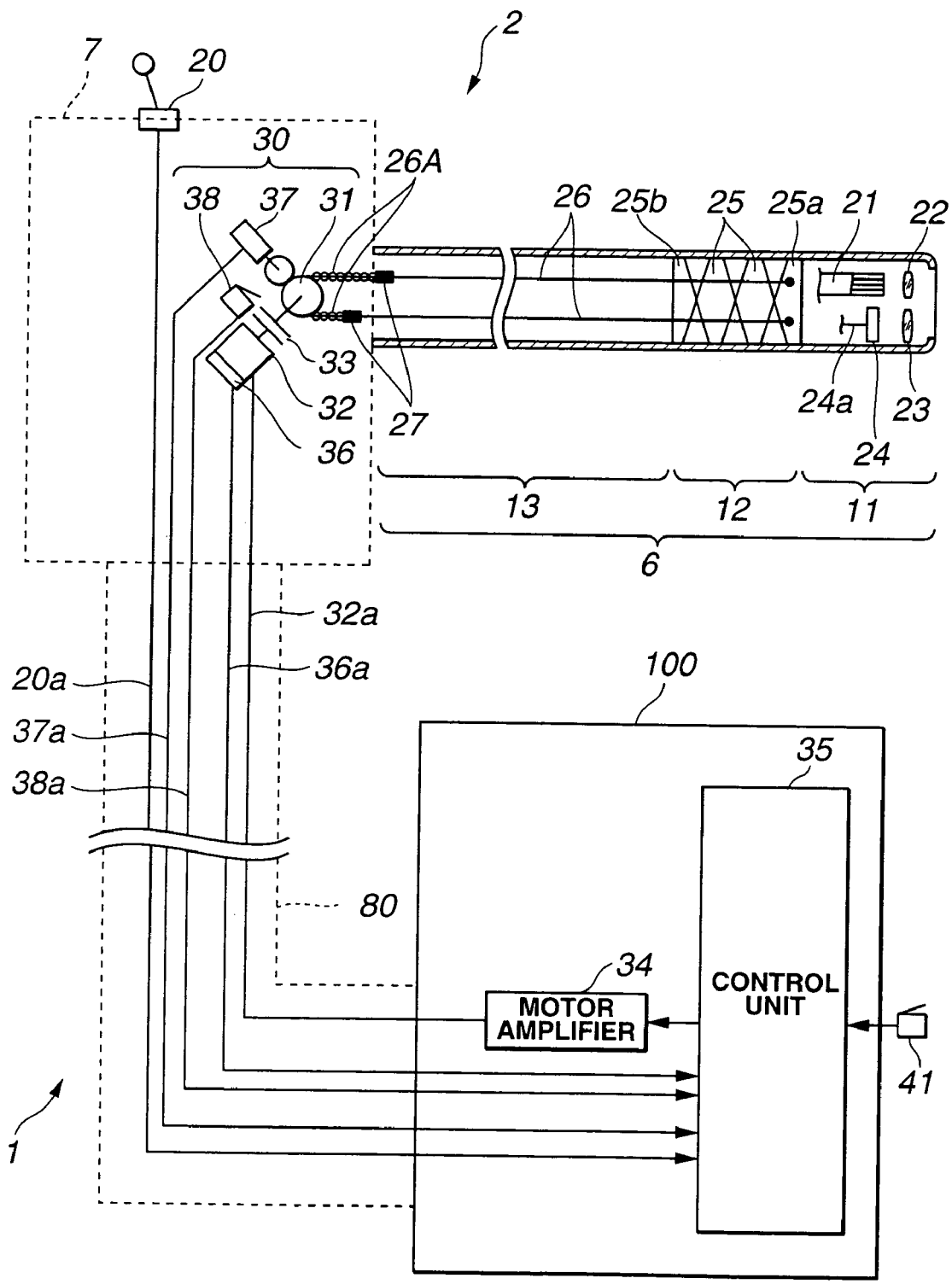
FIG. 4 is a diagram showing the entire structure of an electric bending endoscope apparatus having the electric bending endoscope according to the first embodiment.
Figure 5:
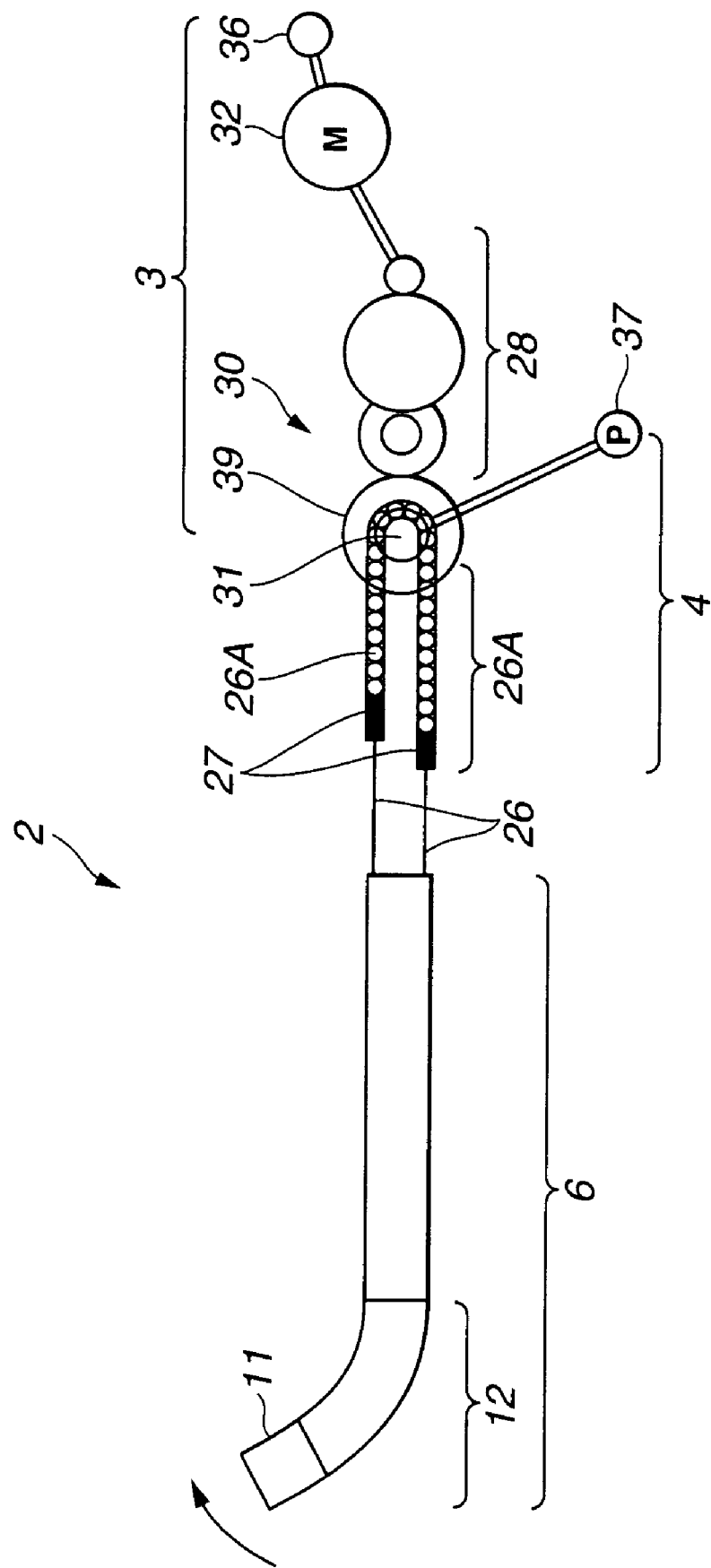
FIG. 5 is a diagram schematically showing main portions of the electric bending endoscope shown in FIG. 4 formed as units.
Figure 6:
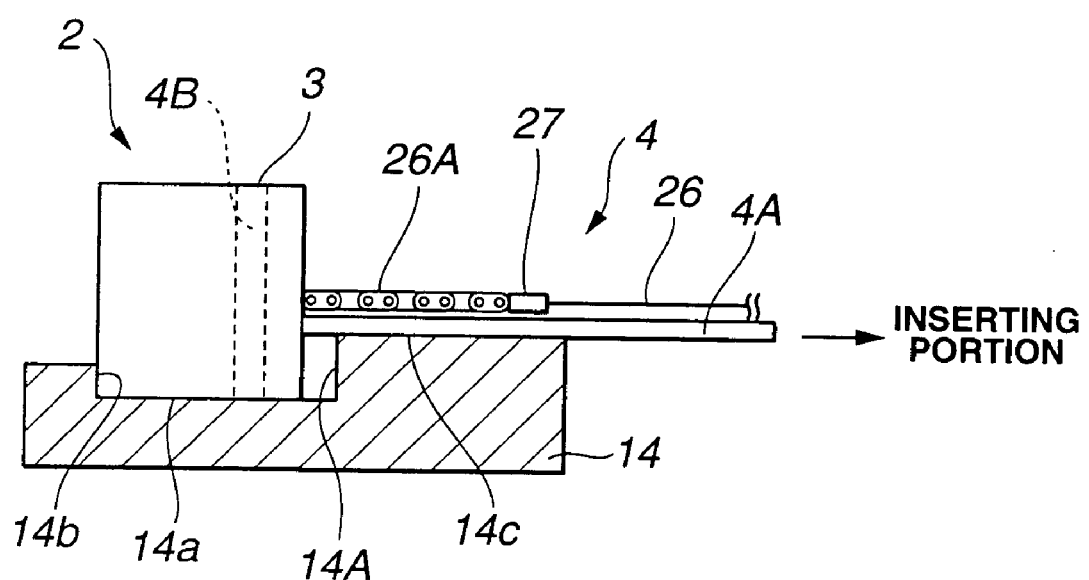
FIG. 6 is a cross-sectional view showing an attaching state of a gear box and a bending and stretch mechanism portion by using a tool, describing the operation, according to the first embodiment.
Figure 7:
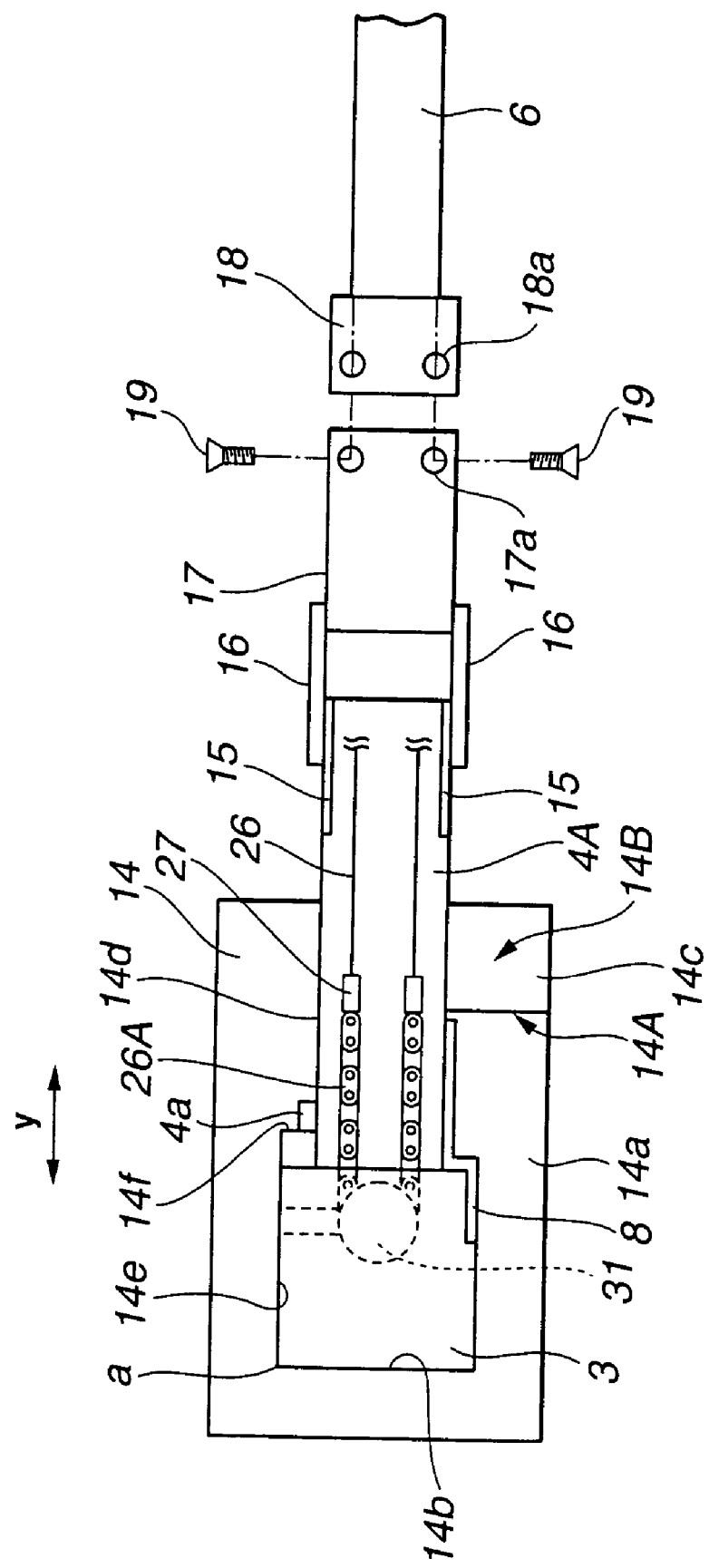
FIG. 7 is a plan view showing an attaching state of the bending and stretch mechanism portion including an inserting portion, describing the operation, according to the first embodiment.

FIGS. 1 to 7 show an electric bending endoscope according to a first embodiment of the present invention. FIG. 1 is an exploded perspective view showing the schematic structure of an electric bending endoscope according to the first embodiment. FIG. 2 is a perspective view schematically showing the electric bending endoscope shown in FIG. 1 after assembling, including a cut-off part. FIG. 3 is a plan view showing the electric bending endoscope shown in FIG. 2. FIG. 4 is a diagram showing the entire structure of an electric bending endoscope apparatus having the electric bending endoscope according to the first embodiment. FIG. 5 is a diagram schematically showing a main portion of the electric bending endoscope shown in FIG. 4 as a unit. FIGS. 6 and 7 are diagrams for explaining a method for attaching a gear box and a bending and stretch mechanism portion in the electric bending endoscope. FIG. 6 is a cross-sectional view showing an attaching state of the gear box and the bending and stretch mechanism portion by using a tool. FIG. 7 is a plan view showing an attaching state of the bending and stretch mechanism portion including an inserting portion.

First, a description is given of the system structure of an electric bending endoscope apparatus having the electric bending endoscope of the present invention with reference to FIG. 4.

Referring to FIG. 4, an electric bending endoscope apparatus 1 having an electric bending endoscope 2 comprises a bending driving portion 30 for electrically bending a bending portion 12, arranged to the edge of an inserting portion 6, a light source device (not shown) for supplying illumination light to the electric bending endoscope 2, a video processor (not shown) for performing signal processing for image pick-up means incorporated in the electric bending endoscope 2, and a bending control device 100 for controlling the driving operation of the bending driving portion in the electric bending endoscope 2. Incidentally, the video processor is connected to a monitor (not shown), outputs a video signal to the monitor, and displays an endoscope image.

Figure 17:
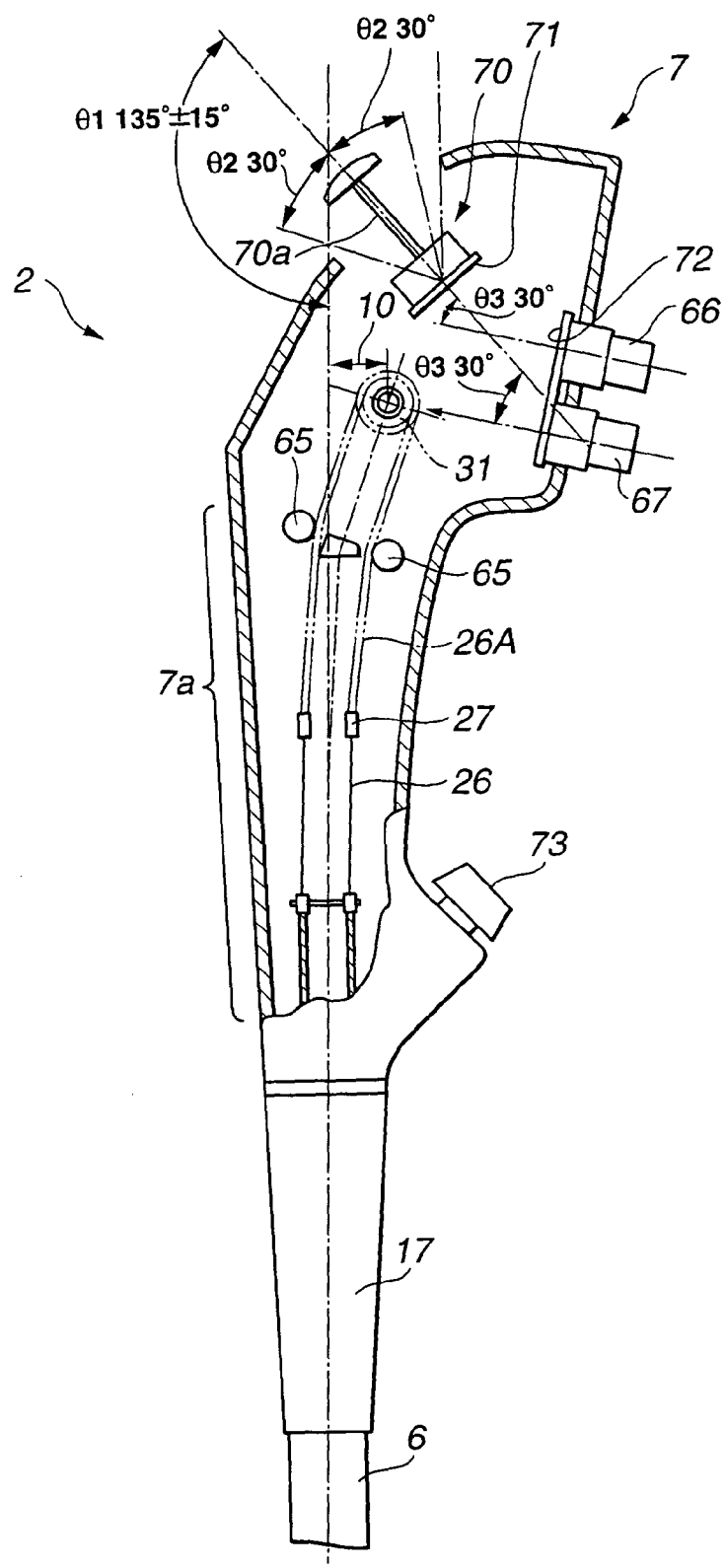
FIG. 17 is a cross-sectional view showing the layout of a bending and stretch mechanism and switches in the operating portion provided for the electric bending endoscope of the present invention.

The electric bending endoscope 2 is continuously arranged to a base end of the inserting portion 6 and comprises an operating portion 7 which commonly functions as a grip portion 7a (refer to FIG. 17). The electric bending endoscope 2 has a soft universal cord 80 extending from a side portion at the operating portion 7.

A light guide or various signal cables (which are not shown) are inserted in the universal cord 80. A connector portion (not shown) is arranged to an end portion of the universal cord 80. Connecting cables from the light source device and the video processor (not shown) and a connecting cable from the bending control device 100 are connected to the universal cord 80, via the connector portion.

Continuously arranged to the inserting portion 6 of the electric bending endoscope 2 is a hard edge portion 11 arranged to the edge thereof, a bending portion 12 which is arranged to a base end side of the edge portion 11 and is freely bent, and a flexible tube portion 13 which is long and flexible and is arranged to a base end side of the bending portion 12.

The operating portion 7 of the electric bending endoscope 2 includes the grip portion 7a (refer to FIG. 17) as a portion which is gripped by a user. In the operating portion 7, a plurality of video switches (not shown) for remote control of the video processor is arranged at an upper portion of the grip portion 7a. Arranged to a side surface of the operating portion 7 are an air and water supply button 66 for operating the air and solution supply operation and a suction button 67 for a suction operation (refer to FIG. 17).

Further, a therapeutic instrument inserting slit 73 (refer to FIG. 17) for inserting a therapeutic instrument such as a biopsy clamp is arranged near a front end of the grip portion 7a of the operating portion 7. The therapeutic instrument inserting slit 73 is connected to a channel for inserting the therapeutic instrument (not shown). A therapeutic instrument such as a clamp (not shown) is inserted in the therapeutic instrument inserting slit 73, the edge of the therapeutic instrument is projected from the opening of the channel formed to the edge portion 11 via the channel for inserting the therapeutic instrument for biopsy, and the biopsy is performed.

The operating portion 7 comprises a bending operation input portion 20 for inputting the operation for bending the bending portion 12 such as a joystick and a track ball.

Further, a specific description is given of the electric bending endoscope 2. A light guide 21 for transmitting the illumination light is inserted in the inserting portion 6 in the electric bending endoscope 2. The light guide 21 reaches the connector portion of the universal cord 80 via the operating portion 7 from the base end side so as to transmit the illumination light from a light source lamp (not shown) arranged in the light source device. The illumination light transmitted from the light guide 21 illuminates a subject such as an affected part of the body from an edge surface of an illumination window (not shown) fixed to the edge portion 11 of the inserting portion via an illumination optical system 22.

An illuminated subject image is captured from an observation window (not shown) arranged adjacently to the illumination window. The captured subject image is picked up by an image pick-up device 24 such as a CCD (Charge-Coupled Device) via an objective optical system 23 and is photoelectrically converted into an image pick-up signal. The image pick-up signal is transmitted via a signal cable 24a extending from the image pick-up device 24, reaches the video connector of the universal cord 80 via the operating portion 7, and is outputted to the video processor (not shown) via the connecting cable 4a. The video processor processes the image pick-up signal from the image pick-up device 24 in the electric bending endoscope 2, generates a standard video signal, and displays the endoscope image on a monitor.

A bending piece 25a at the front end of rotatably connected bending pieces 25 forming the bending portion 12 is connected to a base end portion of the edge portion 11 of the inserting portion in the electric bending endoscope 2. A bending piece 25b at the final end of the bending pieces 25 is connected to an edge side of the flexible portion 13.

A bending operation wire 26 is inserted in the inserting portion 6 to bend the bending portion 12 in the vertical and horizontal directions of an observation field of view. The edge of the bending operation wire 26 is fixed and held to the bending piece 25a at the front end by wax at positions corresponding to the vertical and horizontal directions of the bending portion 12. Referring to FIG. 5, the bending portion 12 is bent in a desired direction and the edge portion 11 is positioned in a desired direction by stretching and contracting the bending operation wire 26 in accordance with the directions.

The bending operation wire 26 is connected to a chain 26A via a connecting portion 27 in a bending and stretch mechanism portion 4, and is stretched and contracted by the bending driving portion 30, thereby electrically bending the bending portion 12 (refer to FIG. 5). The two bending operation wires 26 or the two chains 26A are shown in the vertical or horizontal direction in FIGS. 4 and 5.

The bending driving portion 30 comprises the gear box 3 as a unit indicating the feature of the first embodiment and the bending and stretch mechanism portion 4 connected and fixed to the gear box 3 as a unit.

Referring to FIG. 5, the bending and stretch mechanism portion 4 comprises a sprocket 31 which winds the base end portion of the chain 26A for fixing and holding and which stretches and contracts the chain 26A, and a final gear 39 which is coaxially supported to the sprocket 31 and which transmits the driving force from a motor 32. The gear box 3 comprises the motor 32 for rotating the sprocket 31, and a decelerating gear train (also referred to as a gear train) 28 which transmits the driving force of the motor 32 to the final gear 39 and which decelerates the rotating speed of the motor 32 to generate large torque.

In (the bending driving portion 30 of) the gear box 3, a clutch 33 for disconnecting the driving force of the motor 32 is arranged between the sprocket 31 and the motor 32. Thus, (the bending driving portion 30 of) the gear box 3 disconnects the transmission of the driving force of the motor 32 by using the operation of the clutch 33 and enables a free operation of the angle. The clutch 33 is operated under the control of a control portion 35 arranged to the bending control device 100. The clutch 33 may manually be operated.

A signal line 32a is extending from the motor 32 in the gear box 3. The motor 32 in the gear box 3 receives a motor driving signal from a motor amplifier 34 arranged to the bending control device 100 via a connecting cable 32a in the universal cord 80. The motor amplifier 34 is connected to the control portion 35 and is controlled by the control portion 35.

The motor 32 comprises an encoder 36 which detects a rotating position as means for detecting the rotating position. A signal line 36a extending from the encoder 36 in the universal cord 80 is connected to the control portion 35. The encoder 36 outputs to the control portion 35, a rotating position signal indicating the detected rotating position of the motor 32.

The sprocket 31 in the bending and stretch mechanism portion 4 converts the rotation of the motor 32 into advancing and returning motion of the chain 26A. A potentiometer 37 for detecting the rotating position as the means for detecting the rotating position is connected to the sprocket 31. A signal line 37a extending from the potentiometer 37 in the universal cord 80 is connected to the control portion 35.

Thus, the potentiometer 37 outputs to the control portion 35, a rotating position signal indicating the detected rotating position of the sprocket 31.

Reference numeral 38 denotes a switch for detecting a clutch operation and detects whether the clutch 33 is ON or OFF. A signal line 38a extending from the switch 38 for detecting the clutch operation in the universal cord 80 is connected to the control portion 35. Consequently, the switch 38 for detecting the clutch operation outputs to the control portion 35, a clutch operation signal indicating the detected operation of the clutch 33.

As mentioned above, the bending operation input portion 20 such as the joystick or the track ball is arranged to the grip portion 7a of the operating portion 7 in the electric bending endoscope 2. The signal line 20a extending from the bending operation input portion 20 in the universal cord 80 is connected to the control portion 35. As a result, the bending operation input portion 20 outputs to the control portion 35, a bending operation signal indicating the inputted bending operation.

The control portion 35 controls the motor amplifier 34 and drives the motor 32 in accordance with the bending operation signal from the bending operation input portion 20 based on the signals from the encoder 36 and the potentiometer 37 as the means for detecting the rotating position, thereby bending the bending portion 12.

To accomplish the above objects, the electric bending endoscope 2 used for the electric bending endoscope apparatus 1 with the above-mentioned structure is devised. The devised electric bending endoscope 2 will be described according to the first embodiment with reference to FIGS. 1 to 3.

According to the first embodiment, referring to FIG. 1, the electric bending endoscope 2 comprises the gear box 3 and the bending and stretch mechanism portion 4 forming the bending driving portion 30 for bending the bending portion 12 which are detachably formed as units, respectively.

As mentioned above, the operating portion 7 (refer to FIG. 4) accommodates the gear box 3 and the bending and stretch mechanism portion 4.

Referring to FIGS. 2 and 3, the gear box 3 mainly comprises an outer gear frame 9 forming the external view of the gear box 3 and an inner gear frame 10 accommodated in the outer gear frame 9.

The inner gear frame 10 is made of a hard material, e.g., aluminum diecast, coaxially supports the motor 32, and builds in the encoder 36 and the potentiometer 37. Further, although not shown, the bending input portion 20 such as the joystick is fixed to the inner gear frame 10 via a connecting member on the top surface.

The decelerating gear train 28 (not shown in FIGS. 1 and 2) is arranged to the side surfaces on both sides of the inner gear frame 10. The driving force of the motor 32 is transmitted to the final gear 39 (refer to FIG. 5) in the bending and stretch mechanism portion 4 via the decelerating gear train 28.

As shown in FIGS. 2 and 3, the bending portion 12 comprises two motors 32, two encoders 36, and two potentiometers 37 so as to be bent in the vertical direction or in the horizontal direction. Corresponding thereto, two decelerating gear trains 28, two final gears 39, and two sprockets 31 are provided. Further, according to the first embodiment, the bending portion 12 may be bent in the vertical direction or in the horizontal direction by providing one motor 32, one encoder 36, and one potentiometer 37 and, corresponding thereto, by one decelerating gear train 28, one final gear 39, and one sprocket 31.

The inner gear frame 10 has, on the top surface, a connecting and fixing member 8 for fixing the main frame 4A as a main part of the bending and stretch mechanism portion 4, which will be described later.

The outer gear frame 9 for accommodating the inner gear frame 10 has, on the bottom side of the inserting portion 6, a pair of an attaching hole 3B and a guide portion 3b as fixing means for connecting and fixing the bending and stretch mechanism portion 4 or the rotating shaft 4B as a unit. Further, the outer gear frame 9 has, on the side surface of the side of the bending and stretch mechanism portion 4 therein, an opening 3A for fitting to the bending and stretch mechanism portion 4. The attaching hole 3B, formed with a predetermined diameter, guides and accommodates the rotating shaft 4B in the bending and stretch mechanism portion 4 via the guide portion 3b formed by being notched from the bottom surface side of the outer gear frame 9, and coaxially supports the rotating shaft 4B by the fitting of a positioning and fixing portion 5.

Referring to FIG. 1, the positioning and fixing portion 5 comprises: an attaching hole 5b for being fit into the rotating shaft 4B; a positioning piece 5a which is arranged to be projected to the inner surface side and which is R-shaped matching the inner peripheral surface of the attaching hole 3B; and at least three positioning pins 5c which are arranged in the outer-peripheral direction and which are fit into three positioning holes 3a formed near the attaching hole 3B of the outer gear frame 9.

When the rotating shaft 4B is connected and fixed to the gear box 3, the bending and stretch mechanism portion 4 is fit into the opening 3A, and the rotating shaft 4B is accommodated in the attaching hole 3B. Simultaneously, a base end portion of the rotating shaft 4B is fit into the attaching hole 5b of the fixing portion 5 from both sides thereof, and the positioning piece 5a is fit into the inner-peripheral portion of the attaching holes 3B so as to position the rotating shaft 4B to the gear box 3. Further, the positioning pin 5a is fit into the positioning hole 3a for the connection and fixing. Thus, the positioning operation is accurately performed and, thus, the final gear 39 coaxially arranged to the rotating shaft 4B is accurately engaged and connected to a low-speed gear train 28 (not shown in FIG. 1).

Referring to FIGS. 1 and 3, the bending stretch mechanism portion 4 has the rotating shaft 4B on a base end side thereof. A subframe 4C and the main frame 4A as the main frame member are attached near the center of the rotating shaft 4B. A pair of sprockets 31 and a pair of final gears 39 are arranged to both sides of the bending and stretch mechanism portion 4 to coaxially be supported by the rotating shaft 4B. Therefore, the sprocket 31 and the final gear 39 are rotated integrally with the rotating shaft 4B. The rotating shaft 4B and the main frame 4A may not directly be fixed. That is, the rotating shaft 4B and the main frame 4B are formed independently, and are formed as a part of the components of the gear box 3 which is detachably attached thereto. In this case, the main frame 4A is connected and fixed to the gear box 3 by using only the connecting and fixing member 8.

As shown in FIGS. 1 and 3, when the subframe 4C has two bending and stretch paths, the subframe 4C is arranged to partition the chain 26A for engagement with the sprocket 31. Upon bending the bending portion 12, the stretch operation of the chain 26A is accurately performed without the contact state of the chain 26A with the bending portion 12.

The main frame 4A is the main frame member of the bending and stretch mechanism portion 4, and is plate-shaped with proper intensity. The main frame 4A is arranged to the subframe 4C at a predetermined interval. Referring to FIGS. 2 and 3, a bending portion 4a is formed near a portion for connecting the main frame 4A to the gear box 3 therein. The connecting and fixing member 8 is fixed to the bending portion 4a by screwing a screw 8b, thereby making the stronger connecting and fixing state of the main frame 4A and the gear box 3.

In this case, another end portion of the connecting and fixing portion 8 is arranged to the top surface of the inner gear frame 10 as a hard member, and is fixed to the inner gear frame 10 by the screw operation of the screw 8a.

The connecting and fixing member 8 is made of a hard member such as a stainless member for the purpose of obtaining the intensity. Further, the intensity of the connecting and fixing member 8 may be improved by property changing the thickness or width.

According to the first embodiment, referring to FIGS. 1 and 2, the outer gear frame 9 covers the inner gear frame 10 which is built in. However, the outer gear frame 9 is not limited to this and may have neither top surface nor bottom surface of the outer gear frame 9 so as to expose the inner gear frame 10 to which the connecting and fixing member 8 is fixed so as to improve the maintenance and the assembly (refer to FIG. 10).

Next, a detailed description is given of the operations which is a feature of the electric bending endoscope 2 with reference to FIGS. 1 to 3 and 6 and 7.

It is assumed that in the electric bending endoscope 2 shown in FIG. 2, the maintenance of the bending and stretch mechanism portion 4 is necessary and the bending and stretch mechanism portion 4 is replaced with a new one.

In this case, referring to FIG. 1, in the electric bending endoscope 2 according to the first embodiment, the gear box 3 and the bending and stretch mechanism portion 4 are structured as the units, respectively. Thus, referring to FIG. 2, the connecting and fixing member 8 for connecting and fixing the gear box 3 an the bending and stretch mechanism portion 4 is detached. That is, screws 8a and 8b for fixing the connecting and fixing member 8 to the inner gear frame 10 and the main frame 4A are rotated and detached, thereby detaching the connecting and fixing member 8.

Next, the bending and stretch mechanism portion 4 is detached from the gear box 3. Namely, the positioning and fixing portions 5 for fixing and holding the rotating shaft 4B of the bending and stretch portion 4 to the outer gear frame 9 is detached from the attaching holes 3B, thereby resetting the fixing and holding state of the rotating shaft 4B. Further, the rotating shaft 4B is moved to the opening side of the guide portion 3b, thereby resetting the engaging state between the low-speed gear train 28 in the gear box 3 and the final gear 39 in the bending and stretch mechanism portion 4. The bending and stretch mechanism portion 4 is completely detached from the gear box 3.

When the rotating shaft 4B is formed independently of the bending and stretch mechanism portion 4 and is formed as a part of the components of the gear box 3, the rotating shaft 4B is attached to the gear box 3 and only the connecting and fixing member 8 for connecting the gear box 3 to the main frame 4A of the bending and stretch mechanism portion 4 is detached, and the chain 26A is detached from the operation bending wire 26, thereby detaching the bending and stretch mechanism portion 4 from the gear box 3. That is, the bending and stretch mechanism portion 4 can be exchanged without the detachment of the rotating shaft 4B from the gear box 3.

The detached bending and stretch mechanism portion 4 is replaced with the new bending and stretch mechanism portion 4. Unlikely the conventional technology by which the entire bending operation devices in the operating portion are resolved and the expensive gear box 3 is replaced though it has relatively long life, only the inexpensive bending and stretch mechanism portion 4 which has relatively a short life and inexpensive is easily detached and replaced.

Next, it is assumed that the exchanged new bending mechanism portion 4 is connected and fixed to the gear box 3. In this case, reversed operation of the detachment of the bending and stretch mechanism portion 4 may be executed.

That is, the rotating shaft 4B of the bending and stretch mechanism portion 4 is enclosed in the attaching hole 3B of the gear box 3, the base end portions on both sides of the rotating shaft 4B are fit into the attaching hole 5b of the positioning and fixing portion 5, and the positioning piece 5a is fit into the inner-peripheral surface thereof, thereby positioning the rotating shaft 4B to the gear box 3. Further, the positioning pin 5 is fit into the positioning hole 3a, thereby executing the connection and fixing. Thus, the low-speed gear train 28 in the gear box 3 is engaged with and is connected to the final gear 39 in the bending and stretch mechanism portion 4.

When the rotating shaft 4B is formed independently of the bending and stretch mechanism portion 4 and is formed as a part of the components of the gear box 3, the rotating shaft 4B is attached to the gear box 3 and the chain 26A in the bending and stretch mechanism portion 4 is engaged with the sprocket 31 in the rotating shaft 4B and the chain 26A comes into contact with the operation bending wire 26. After that, the main frame 4A in the bending and stretch mechanism portion 4 is positioned to the gear box 3 and the bending and stretch mechanism portion 4 is connected and fixed to the gear box 3 by using the connecting and fixing member 8.

Preferably, the bending and stretch mechanism portion 4 is positioned and fixed to the gear box 3 at the position at which the loss is minimum when the driving force of the motor 32 is transmitted to the advance and return of the chain 26A and the bending operation wire 26.

According to the first embodiment, in order to satisfy the above requirements, referring to FIGS. 6 and 7, the bending and stretch mechanism portion 4 is positioned to the gear box 3 with high accuracy by using the positioning tool 14 for the connecting and fixing.

Referring to FIGS. 6 and 7, the positioning tool 14 is made of a cubic-shaped hard member having four planes different heights, and comprises grooves 14A for regulating the gear box forming the first and second lower planes and grooves 14B for regulating the bending and stretch mechanism portion forming the third and fourth planes higher than the first and second ones.

The groove 14A for regulating the gear box regulates three directions (x-, y-, and z-directions) of the gear box 3, and comprises: a first regulating surface 14a for slidably moving the gear box 3 and for regulating the vertical direction (z-direction) of the gear box 3; a second regulating surface 14b which is vertical to the first regulating surface 14a and which regulates the longitudinal direction (y-direction) of the gear box 3; and a third regulating surface 14e which is vertically arranged to the second regulating surface 14b and which regulates the horizontal direction (x-direction) of the gear box 3.

The groove 14B for regulating the bending and stretch mechanism portion comprises: a fourth regulating surface 14c which has the main frame 4A of the bending and stretch mechanism portion 4 thereon and which regulates and supports the gear box 3 in the vertical direction (z-direction); a fifth regulating surface 14d which is vertical to the fourth regulating surface 14c and which regulates the horizontal direction (x-direction) of the main frame 4A; and a sixth regulating surface 14f which regulates the longitudinal direction (y-direction) of the main frame 4A of the bending and stretch mechanism portion 4 to the gear box 3.

A regulating portion 4a for regulating the position of the main frame 4A to the gear box 3 is formed by making a part of the side surface of the edge of the main frame 4 contact with the sixth regulating surface 14f.

The height dimension of the fourth regulating surface 14c (difference in height from the first regulating surface 14a) is previously set at the best fixing position to the gear box 3.

It is assumed that the bending and stretch mechanism portion 4 is positioned to the gear box 3 by using the positioning tool 14 for the connecting and fixing. In this case, referring to FIG. 6, the gear box 3 is placed onto the groove 14A for regulating the gear box in the positioning tool 14, and the bending and stretch mechanism portion 4 fixed to the gear box 3 is placed onto the groove 14B for the bending and stretch mechanism of the positioning tool 14 by using the positioning and fixing portion 5.

In this state, the gear box 3 is slid onto the first regulating surface 14a and brought into contact with the second and third regulating surfaces 14d and 14e. Further, the main frame 4A of the bending and stretch mechanism portion 4 is slid onto the fourth regulating surface 14c and brought into contact with the fifth regulating surface 14d. Furthermore, the regulating portion 4a of the main frame 4A comes into contact with the sixth regulating surface 14f. Consequently, the main frame 4A of the bending and stretch mechanism portion 4 is positioned to the gear box 3 in the x-, y-, and z-directions thereof with ease and continuous high-accuracy, irrespective of the manual operation of the operator.

After that, the main frame 4A of the bending and stretch mechanism portion 4 is fixed to the gear box 3 by using the connecting and fixing member 8 so that the positioning state is maintained and the bending and stretch mechanism portion 4 is strongly connected to the gear box 3. Namely, one end portion of the connecting and fixing member 8 is fixed onto the inner gear frame 10 as the hard member by the screwing operation of the screw 8a, and the other end portion of the connecting and fixing member 8 is fixed onto the bending portion 4a of the main frame 4A by the screwing operation of the screw 8b.

The bending and stretch mechanism portion 4 is positioned to the gear box 3 at the position at which the loss becomes minimum upon transmitting the driving force of the motor 32 to the advance and return of the chain 26A and the bending operation wire 26, and the main frame 4A is strongly connected and fixed to the gear box 3.

Thus, since the bending and stretch mechanism portion 4 is connected and fixed to the gear box 3 at the best position, the transmission loss of the driving force is minimum and the motor 32 can be reduced in size as much as possible. As a result, the entire operating portions including the gear box 3 is reduced in size. Further, the gear rate of the low-speed train 28 in the gear box 3 is small and therefore the response performance of the bending operation is improved.

After completing the attachment of the bending and stretch mechanism portion 4, a connecting tube 17 is attached via a substrate 15 and a connecting member 16 which are arranged to the edge portion of the bending and stretch mechanism portion 4. Then, a cap 18 of the inserting portion 6 is fit into the other end side of the connecting tube 17 and the inserting portion 6 is attached by screwing a screw 19 via a screw hole 18a of the cap 18 and via a screw hole 17a of the connecting tube 17.

According to the first embodiment, the inserting portion 6, which is frequently used and to which external force is applied, is connected to the inner gear frame 10 as the hard member of the gear box 3 via the high-intensity members such as the cap 18, the connecting tube 17, the connecting member 16, the main frame 4A of the bending and stretch mechanism portion 4, and the connecting and fixing member 8. Thus, any external force (surplus force) is sufficiently absorbed during operating the electric bending endoscope 2. Then, the tolerance is excessively improved and the transmission loss can be minimum.

According to the first embodiment, the gear box 3 and the bending and stretch mechanism portion 4 are detachably formed as units, respectively. Thus, the simple structure improves the assembly and the maintenance performance and the maintenance costs are reduced in the electric bending endoscope.

The bending and stretch mechanism portion 4 is positioned and fixed to the gear box 3, by using the positioning tool 14, at the position at which the transmission loss of the driving force becomes minimum. The motor 32 can be reduced in size and this contributes to the small size of the entire operating portions including the gear box 3. Further, the gear rate of the low-speed train 28 in the gear box 3 is small and therefore the response performance of the bending operation is improved.

Further, the main frame 4A of the bending and stretch mechanism portion 4 is connected and fixed to the inner gear frame 10 as the hard member via the connecting and fixing member 8. Therefore, any external force (surplus force) is sufficiently absorbed during the operation and the tolerance is excessively improved.

(Second Embodiment)

Figure 8:
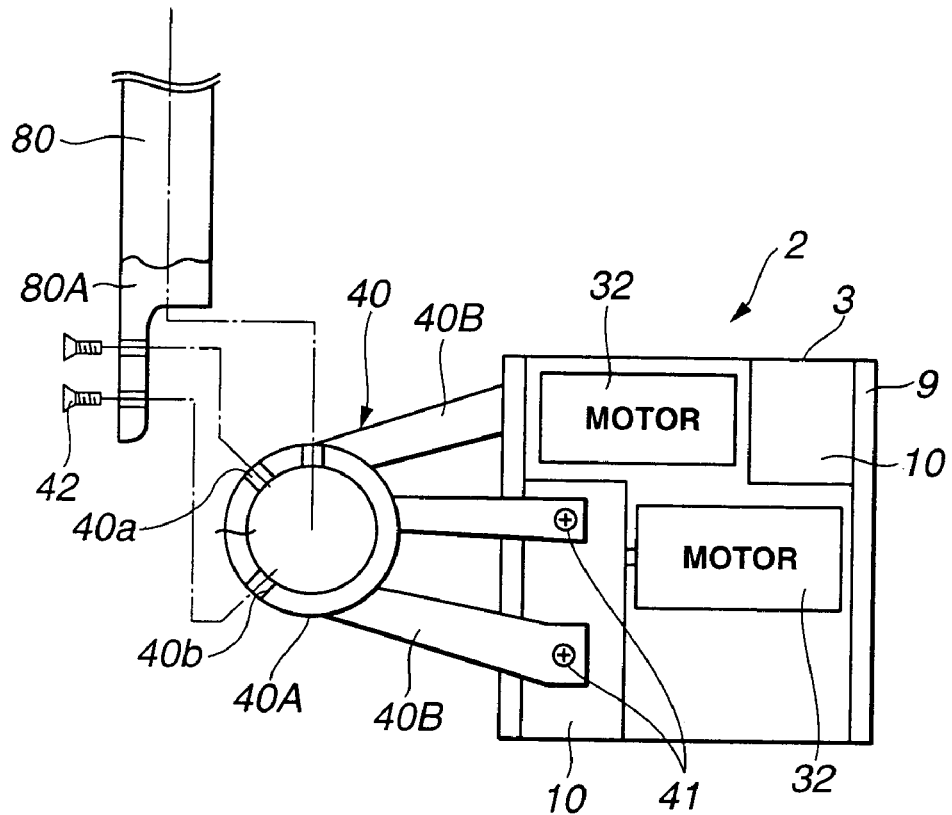
FIG. 8 is a diagram showing the structure of a gear box having a pin used for the electric bending endoscope according to a second embodiment of the present invention.
Figure 9:
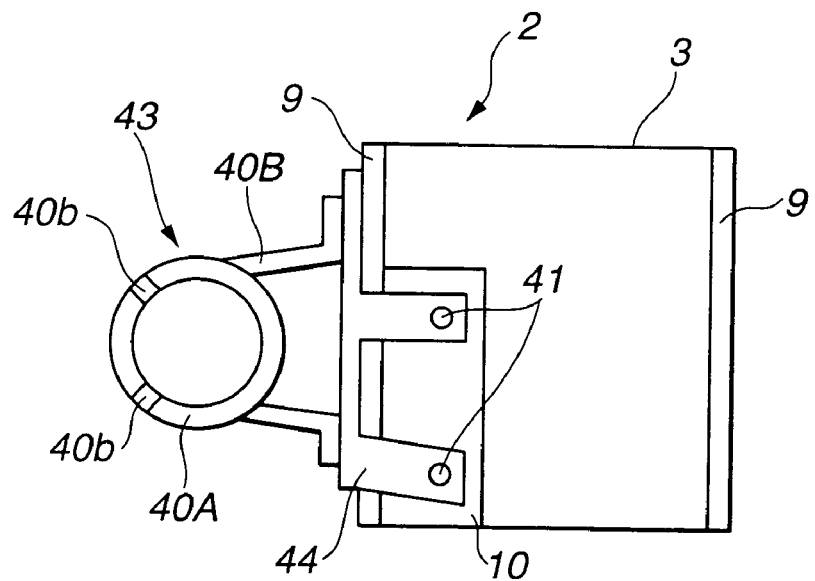
FIG. 9 is a diagram showing the structure of the gear box having the pin according to a modification of the pin shown in FIG. 8.

FIGS. 8 and 9 show an electric bending endoscope according to a second embodiment of the present invention. FIG. 8 is a diagram showing the structure of a gear box having a stop tool used for the electric bending endoscope according to the second embodiment. FIG. 9 is a diagram showing the structure of the gear box having a pin according to a modification of the stop tool shown in FIG. 8. Incidentally, the same components as those of the electric bending apparatus according to the first embodiment are designated by the same reference numerals in FIGS. 8 and 9, a description thereof is omitted, and only different portions are described.

According to the second embodiment, unlike the first embodiment, holding means for holding the universal cord 80 arranged in the operating portion 7 is fixed to the inner gear frame 10 of the gear box 3.

Specifically, referring to FIG. 8, the outer gear frame 9 of the gear box 3 is formed without the top surface and the bottom surface so that the inner gear frame 10 accommodated therein is exposed. Further, a stop tool 40 as holding means for holding the universal cord 80 is fixed to the inner gear frame 10 as the hard member, by using the screw 41.

In addition, referring to FIG. 8, the stop tool 40 comprises a ring-shaped holding portion 40A to which the universal cord 80 is fit by screwing a screw 42 and a fixing portion 40B which fixes the holding portion 40A to the inner gear frame 10 of the gear box 3 by at least three plate members or stick members.

The holding portion 40A has screw holes 40a and 40b at predetermined positions on the peripheral surface thereof. A connector 80A arranged to the edge portion of the universal cord 80 is fit and the universal cord 80 is fit and is held to the gear box 3 by screwing a screw 42 via a screw hole arranged to the connector 80A and the screw holes 40a and 40b.

Other structure is the same as that according to the first embodiment.

Therefore, according to the second embodiment, the external force (surplus force) is forcedly applied to the universal cord 80 during the operation. The universal cord 80 is fixed and held to the inner gear frame 10 as the hard member of the gear box 3 by using the stop tool 40, thereby absorbing the external force (surplus force) via the universal cord 80. Thus, the tolerance is remarkably improved and the engagement state (connecting state) is best held between the low-speed gear train 28 in the gear box 3 and the final gear 28 of the bending and stretch mechanism portion 4. Thus, the transmission loss of the driving force is reduced and the bending operation performance is preferably obtained. Other advantages are the same as those according to the first embodiment.

According to the modification of the second embodiment, referring to FIG. 8, the stop tool 40 as the holding means may comprise a holding portion 40A for fitting the universal cord 80 a fixing portion 40B which is extended from the holding portion 40A and which is made of two plate members or stick members, and a connecting member 44 which fixes the fixing portion 40B by the screw operation of a screw (not shown) and which fixes the fixing portion 40 to the inner gear frame 10 of the gear box 3, so that the universal cord 80 is fixed and held. In this case, the same advantages as those according to the first embodiment are obtained.

In the electric bending endoscope 2 with the simple structure according to the invention, the main frame 4A of the bending and stretch mechanism portion 4 is positioned to the gear box 3 with high accuracy for the connection and fixing. An electric bending endoscope will be described according to a third embodiment with reference to FIGS. 10 to 15.

(Third Embodiment)

Figure 10:
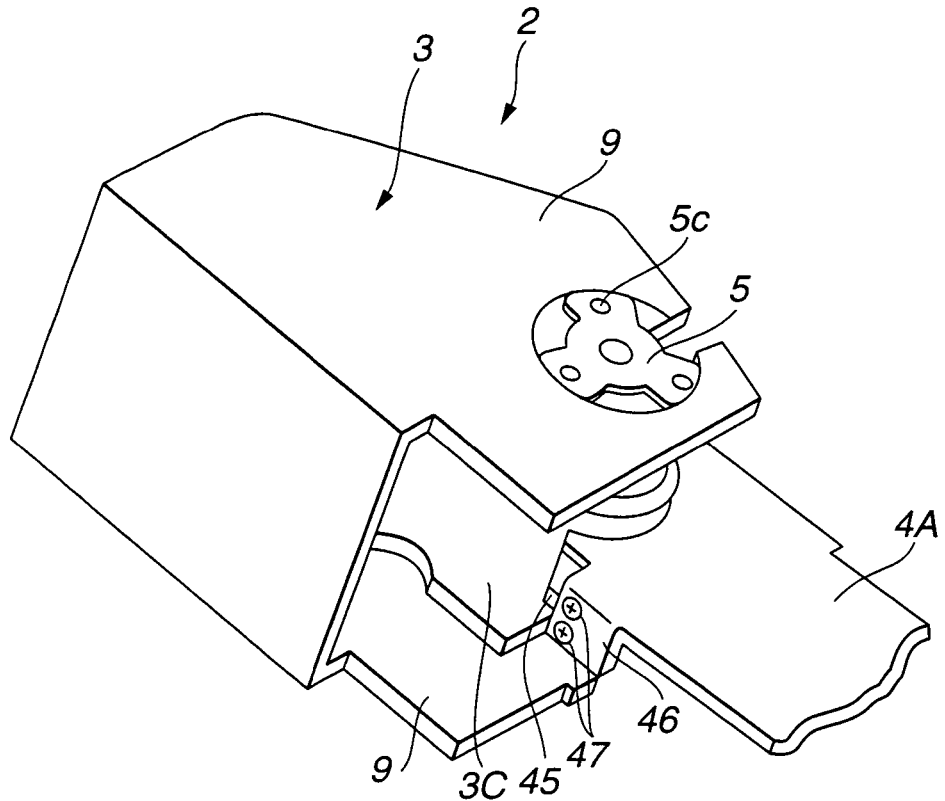
FIG. 10 is a perspective view showing the structure of a gear box, which is used for an electric bending scope and to which a main frame is fixed, according to a third embodiment of the present invention.
Figure 11:
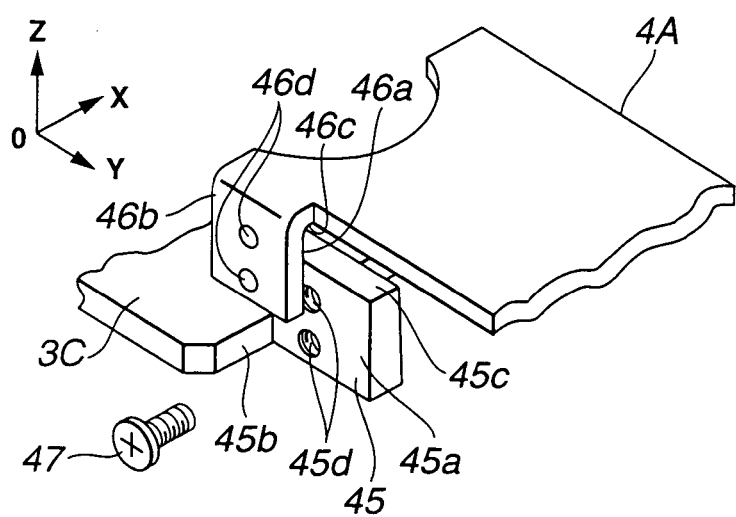
FIG. 11 is a perspective view showing an example of the structure of positioning and fixing means shown in FIG. 10.

FIGS. 10 and 11 show an electric bending endoscope according to the third embodiment of the present invention. FIG. 10 is a perspective view showing the structure of a gear box, which is used for an electric bending scope and to which a main frame is fixed, according to a third embodiment of the present invention. FIG. 11 is a perspective view showing an example of the structure of positioning and fixing means shown in FIG. 10. Incidentally, the same components as those of the electric bending apparatus 2 shown according to the first embodiment are designated by the same reference numerals and are not described, and only different portions are described.

According to the third embodiment, positioning and fixing means is arranged to the connecting portion of the gear box 3 and the main frame 4A in the bending and stretch mechanism portion 4, and positions and fixes with high accuracy in three-axis directions (vertical direction (z-direction), horizontal direction (x-direction), and longitudinal direction (y-direction)) of the main frame 4A to the gear box 3.

Referring to FIG. 10, specifically, a bending and fixing portion 46 as the positioning and fixing means for fixing the gear box 3 is arranged to the base end portion of the gear box 3 side in the main frame 4A of the bending and stretch mechanism portion 4.

The bending and fixing portion 46 comprises an extending portion of the main frame 4A, which is vertically bent, regulates the three-axis directions (x-, y-, and z-directions)

of the main frame 4A upon positioning the gear box 3, and further has a first regulating surface 46c for regulating the vertical direction (z-direction) of the main frame 4A, a second regulating surface 46b for regulating the longitudinal direction (y-direction) of the main frame 4A, a third regulating surface 46a for regulating the horizontal direction (x-direction) of the main frame 4A, and two circular holes 46d for fixing the main frame 4A to the gear box 3.

On the other hand, the gear box 3 which is engaged with the bending and fixing portion 46 has a projecting and fixing portion 45 as the positioning and fixing means at the base end portion of an extending portion 3C extended to the main frame 4A side of the inner gear frame 10 as the hard member.

The projecting and fixing portion 45 is arranged so that a plate-shaped member is projected in the y-direction and the vertical direction (z-direction) from the base end portion of the inner gear frame 10, and comprises a fourth regulating surface 45c which comes into contact with the first regulating surface 46c of the bending and fixing portion 46, a fifth regulating surface 45b which comes into contact with the second regulating surface 46b of the bending and fixing portion 46, a sixth regulating surface 45a which comes into contact with the third regulating surface 46a of the bending and fixing portion 46, and two screw holes 45d for fixing the bending and fixing portion 46.

The regulating surfaces 45a to 46c have an angular relationship of 90° formed thereof each other, corresponding to the three-axis directions. That is, the first regulating surface 46c and the fourth regulating surface 45c are vertical to the main frame 4A and the z-direction of the extending portion 3C. The second regulating surface 46b and the fifth regulating surface 45b are vertical to the main frame 4A and the y-direction of the extending portion 3C. The third regulating surface 46a and the sixth regulating surface 45a are vertical to the main frame 4A and the x-direction of the extending portion 3C.

In the electric bending endoscope 2 according to the third embodiment, referring to FIG. 11, the main frame 4A of the bending and stretch mechanism portion 4 is positioned to the gear box 3 by engaging the bending and fixing portion 46 of the main frame 4A with the projecting and fixing portion 45 of the gear box 3.

In this case, the first regulating surface 46c of the bending and fixing portion 46 comes into contact with the fourth regulating surface 45c of the projecting and fixing portion 45, the third regulating surface 46a of the bending and fixing portion 46 comes into contact with the sixth regulating surface 45a of the projecting and bending portion 45, and the second regulating surface 46b of the bending and fixing portion 46 comes into contact with the fifth regulating surface 45b of the projecting and fixing portion 45. Consequently, the three-axis directions (x-, y-, and z-directions) of the main frame 4A are positioned to the extending portion 3C of the gear box 3 with high accuracy.

In this state, the two circular holes 46d of the bending and fixing portion 46 are screwed to the two screw holes 45d of the projecting and fixing portion 45 by using the screws 47, thereby connecting and fixing the main frame 4A to the gear box 3 in the highly-accurately positioned state.

Other structures and operations are the same as those according to the first embodiment.

According to the third embodiment, the same advantages as those according to the first embodiment are obtained. Further, the main frame 4A of the bending and stretch mechanism portion 4 is simply positioned to the gear box 3 with high accuracy for the connecting and fixing. Since the regulating surfaces are pressed and fixed, the intensity for the fixing is high and the positioning and fixing portions are reduced in size. Furthermore, the assembling time is reduced.

(Fourth Embodiment)

Figure 12:
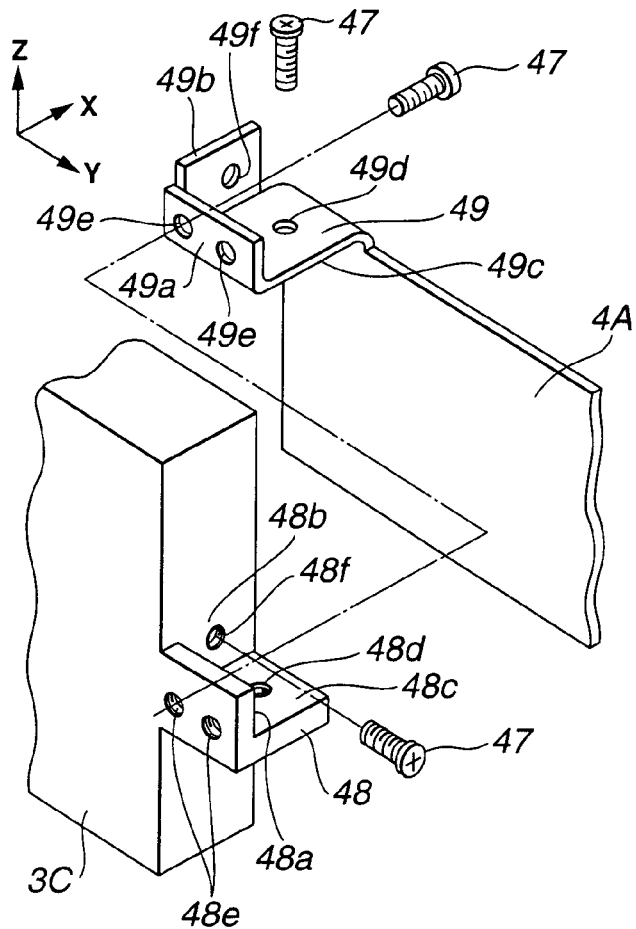
FIG. 12 is a perspective view showing an example of the structure of improved positioning and fixing means in an electric bending endoscope according to a fourth embodiment of the present invention.

FIG. 12 is a perspective view showing an example of the structure of improved positioning and fixing means in an electric bending endoscope according to a fourth embodiment of the present invention. Incidentally, the same components as those of the electric bending apparatus 2 shown according to the third embodiment are designated by the same reference numerals and are not described, and only different portions are described.

According to the fourth embodiment, positioning and fixing means is obtained by devising the positioning and fixing means according to the third embodiment, and positions and fixes with high accuracy in the three-axis directions (vertical direction (z-direction), horizontal direction (x-direction), and longitudinal direction (y-direction)) of the main frame 4A to the gear box 3.

Referring to FIG. 12, a bending and fixing portion 49 as the positioning and fixing means for fixing the gear box 3 is arranged to the base end portion of the gear box 3 side in the main frame 4A of the bending and stretch mechanism portion 4.

The bending and fixing portion 49 comprises an extending portion of the main frame 4A, which is vertically bent and is box-shaped, regulates the three-axis directions (x-, y-, and z-directions) of the main frame 4A upon positioning the gear box 3, and further has a first regulating surface 49c for regulating the z-direction of the main frame 4A, a second regulating surface 49b for regulating the y-direction of the main frame 4A, a third regulating surface 49a for regulating the x-direction of the main frame 4A, and four circular holes 49d, 49e (two), and 49f for fixing the main frame 4A to the gear box 3, arranged to the first to third regulating surfaces 49a to 49c.

On the other hand, the gear box 3 which is engaged with the bending and fixing portion 49 has a projecting and fixing portion 48 as the positioning and fixing means at the base end portion of an extending portion 3C extended to the main frame 4A side of the inner gear frame 10 as the hard member.

The projecting and fixing portion 48 is L-shaped corresponding to the shape of the bending and fixing portion 49 so that it is projected in the y-direction and the vertical direction (z-direction) from the base end portion of the inner gear frame 10, and comprises a fourth regulating surface 48c which comes into contact with the first regulating surface 49c of the bending and fixing portion 49, a fifth regulating surface 48b which comes into contact with the second regulating surface 49b of the bending and fixing portion 49, a sixth regulating surface 48a which comes into contact with the third regulating surface 49a of the bending and fixing portion 49, and four screw holes 48d, 48e (two) and 48f for fixing the bending and fixing portion 49.

The regulating surfaces 48a to 49c have an angular relationship of 90° formed thereof each other, corresponding to the three-axis directions, similarly to the positioning and fixing means according to the third embodiment.

In the electric bending endoscope 2 according to the fourth embodiment, referring to FIG. 12, the main frame 4A of the bending and stretch mechanism portion 4 is positioned and is fixed to the gear box 3 by engaging the bending and fixing portion 49 of the main frame 4A with the projecting and fixing portion 48 of the gear box 3.

In this case, the first regulating surface 49c of the bending and fixing portion 49 comes into contact with the fourth regulating surface 48c of the projecting and fixing portion 48, the third regulating surface 49a of the bending and fixing portion 49 comes into contact with the sixth regulating surface 48a of the projecting and bending portion 48, and the second regulating surface 49b of the bending and fixing portion 49 comes into contact with the fifth regulating surface 48b of the projecting and fixing portion 48. Consequently, the three-axis directions (x-, y-, and z-directions) of the main frame 4A are positioned to the extending portion 3C of the gear box 3 with high accuracy.

In this state, the circular holes 49d of the bending and fixing portion 49 are screwed to the screw holes 48d of the projecting and fixing portion 48 by using pot screws 47, the circular holes 49e are screwed to the screw holes 48e by using the pot screws 47, and the circular holes 49f are screwed to the screw holes 48f by using the pot screws 47. Thus, the main frame 4A is connected and is fixed to the gear box 3 in the highly-accurately positioned state.

The bending and fixing portion 49 may be pressed and be positioned to the projecting and fixing portion 48 by using a stage-shaped tool, thereby performing the fixing operation using the screw operation of the pot screw 47.

Other structures and operations are the same as those according to the third embodiment.

Thus, according to the fourth embodiment, the same advantages as those according to the third embodiment are obtained.

(Fifth Embodiment)

Figure 13:
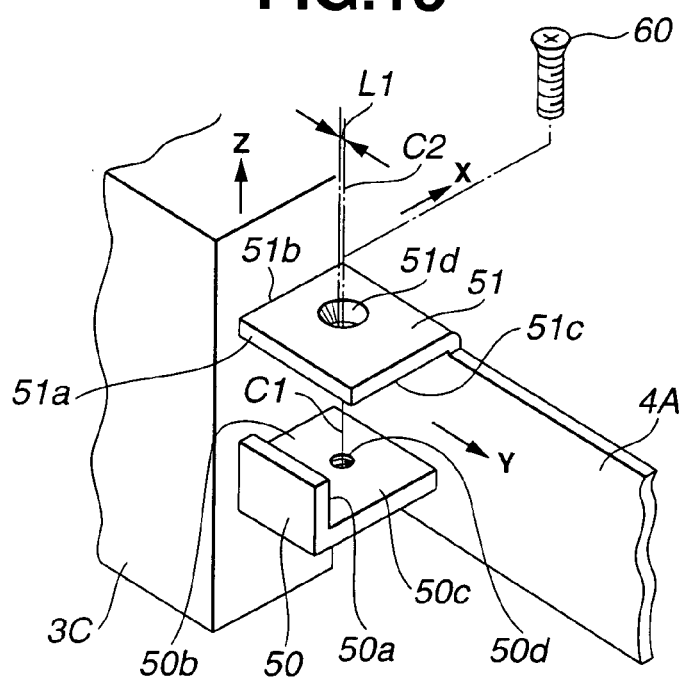
FIG. 13 is a perspective view showing an example of the structure of positioning and fixing means in an electric bending endoscope according to a fifth embodiment of the present invention.

FIG. 13 is a perspective view showing an example of the structure of positioning and fixing means in an electric bending endoscope according to a fifth embodiment of the present invention. Incidentally, the same components as those of the electric bending apparatus 2 shown according to the third embodiment are designated by the same reference numerals and are not described, and only different portions are described.

According to the fifth embodiment, referring to FIG. 13, a bending and fixing portion 51 for fixing to the gear box 3 as positioning and fixing means is arranged to the base end portion on the gear box 3 side in the main frame 4A of the bending and stretch mechanism portion 4.

The bending and fixing portion 51 comprises an extending portion on the base end side in the main frame 4A, which is vertically bent, and regulates three-axis directions (z-, x-, and y-directions) of the main frame 4A to the gear box 3 upon positioning to the gear box 3. The bending and fixing portion 51 further has a first regulating surface 51c for regulating the z-direction of the main frame 4A, a second regulating surface 51b for regulating the y-direction of the main frame 4A, a third regulating surface 51a for regulating the x-direction of the main frame 4A, and a screw hole 51d for fixing the main frame 4A to the gear box 3, arranged substantially to the center of the first regulating surface 51c.

On the other hand, the gear box 3 which is engaged with the bending and fixing portion 49 has a projecting and fixing portion 50 as the positioning and fixing means at the base end portion of an extending portion 3C extended to the main frame 4A side of the inner gear frame 10 as the hard member.

The projecting and fixing portion 48 is L-shaped corresponding to the shape of the bending and fixing portion 49 so that it is projected in the y-direction and the z-direction from the base end portion of the inner gear frame 10, and comprises a fourth regulating surface 50c which comes into contact with the first regulating surface 51c of the bending and fixing portion 51, a fifth regulating surface 50b which comes into contact with the second regulating surface 51b of the bending and fixing portion 51, a sixth regulating surface 50a which comes into contact with the third regulating surface 51a of the bending and fixing portion 51, and a female screw hole 50d for fixing the bending and fixing portion 51, arranged to the center of the fourth regulating surface 50c.

The second and fifth regulating surfaces 51b to 50b are mechanically processed and are formed with an angle of 90° in the x-, y-, and z-directions.

A plate screw hole 51d of the bending and fixing portion 51 is arranged to the first regulating surface 51c so that a center C2 of the plate screw hole 51d is deviated (eccentric) from a center C1 of the female screw hole 50d of the projecting and fixing portion 50 by a predetermined dimension L1 in the y-direction.

In the electric bending endoscope 2 according to the fifth embodiment, referring to FIG. 13, the main frame 4A of the bending and stretch mechanism portion 4 is positioned and is fixed to the gear box 3 by engaging the bending and fixing portion 51 of the main frame 4A with the projecting and fixing portion 50 of the gear box 3.

In this case, the first regulating surface 51c of the bending and fixing portion 51 comes into contact with the fourth regulating surface 50c of the projecting and fixing portion 50, the third regulating surface 51a of the bending and fixing portion 51 comes into contact with the sixth regulating surface 50a of the projecting and bending portion 50, and the second regulating surface 51b of the bending and fixing portion 51 comes into contact with the fifth regulating surface 50b of the projecting and fixing portion 50. Consequently, the three-axis directions (x-, y-, and z-directions) of the main frame 4A are positioned to the extending portion 3C of the gear box 3 with high accuracy. In this state, the center of the plate screw hole 51d of the first regulating surface 51c is deviated from the female screw hole 51d of the fourth regulating surface 50c by the predetermined distance L1.

This state keeps and the screw operation is performed via the screw hole 51d of the bending and fixing portion 51 and the female screw hole 50d of the projecting and fixing portion 50 by using a plate screw 60. Since the plate screw hole 51d has the eccentric structure, the second regulating surface 51b of the main frame 4A is further pressed to the fifth regulating surface 50b. As a result, the main frame 4A is strongly connected and is fixed to the gear box 3 in the highly-accurately positioned state in the three x-, y-, and z-directions.

According to the fifth embodiment, the bending and fixing portion 51 and the projecting and fixing portion 50 are formed like that according to the third embodiment. Further, the main frame 4A may strongly be connected and fixed to the gear box 3 by the positioning with the plate screw hole and the female screw hole at the eccentric position and by the screw operation of the plate screw.

Other structures and operations are the same as those according to the third embodiment.

Thus, according to the fifth embodiment, the same advantages as those according to the third embodiment are obtained. In addition, since the plate screw 47 presses the regulating surfaces without the operator's manual operation, the stable energization force is obtained and the both the positioning and connection and fixing become strong.

(Sixth Embodiment)

Figure 14:
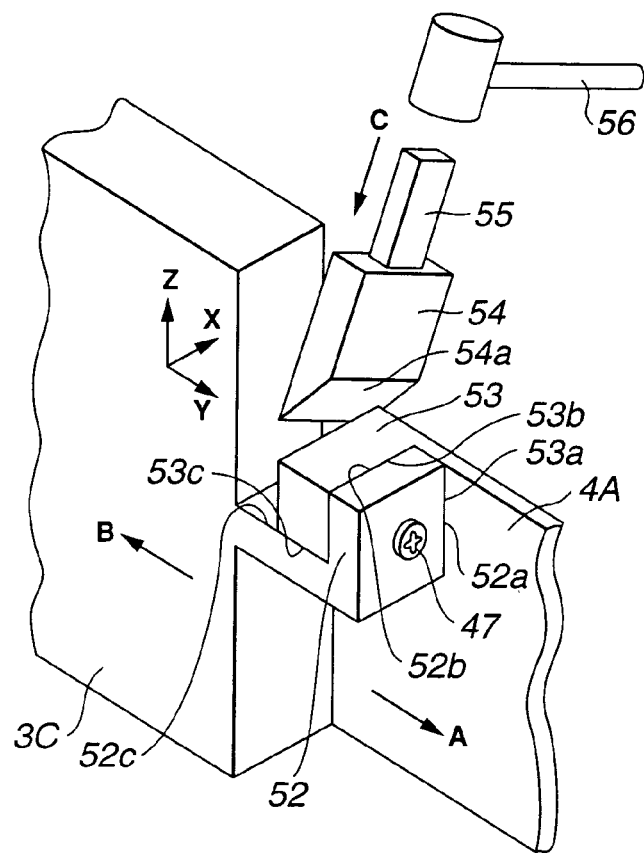
FIG. 14 is a perspective view showing an example of the structure of improved positioning and fixing means in an electric bending endoscope according to a sixth embodiment of the present invention.

FIG. 14 is a perspective view showing an example of the structure of improved positioning and fixing means in an electric bending endoscope according to a sixth embodiment of the present invention. Incidentally, the same components as those of the electric bending apparatus 2 shown according to the third embodiment are designated by the same reference numerals and are not described, and only different portions are described.

According to the sixth embodiment, referring to FIG. 14, the main frame 4A of the bending and stretch mechanism portion 4 is made of a hard member such as aluminum diecast. A bending and fixing portion 53 for fixing to the gear box 3 as positioning and fixing means is arranged to the base end portion on the gear box 3 side in the main frame 4A of the bending and stretch mechanism portion 4.

The bending and fixing portion 53 comprises an extending portion on the base end side in the main frame 4A, which is vertically bent, and regulates three-axis directions (z-direction, y-direction, and x-direction) of the main frame 4A to the gear box 3 upon positioning to the gear box 3. The bending and fixing portion 53 further has a first regulating surface 53c for regulating the z-direction of the main frame 4A, a second regulating surface 53b for regulating the y-direction of the main frame 4A, a third regulating surface 53a for regulating the x-direction of the main frame 4A, and a screw hole (not shown) for fixing the main frame 4A to the gear box 3.

On the other hand, the gear box 3 which is engaged with the bending and fixing portion 53 has a projecting and fixing portion 52 as the positioning and fixing means at the base end portion of an extending portion 3C extended to the main frame 4A side of the inner gear frame 10 as the hard member.

The projecting and fixing portion 52 is L-shaped corresponding to the shape of the bending and fixing portion 53 so that it is projected in the y-direction and the z-direction from the base end portion of the extending portion 3C in the inner gear frame 10, and comprises a fourth regulating surface 52c which comes into contact with the first regulating surface 53c of the bending and fixing portion 53, a fifth regulating surface 52b which comes into contact with the second regulating surface 53b of the bending and fixing portion 53, a sixth regulating surface 52a which comes into contact with the third regulating surface 53a of the bending and fixing portion 53, and a screw hole (not shown) for fixing the bending and fixing portion 53.

The fourth regulating surfaces 52c of the projecting and fixing portion 52 is formed wider than the thickness of the bending and fixing portion 53. That is, when the first regulating surface 53c comes into contact with the fourth regulating surface 52c, a space exists between the fourth regulating surface 52c and the extending portion 3C.

In the electric bending endoscope 2 according to the sixth embodiment, referring to FIG. 14, the main frame 4A of the bending and stretch mechanism portion 4 is positioned and is fixed to the gear box 3, by engaging the bending and fixing portion 53 of the main frame 4A with the projecting and fixing portion 52 of the gear box 3 while the main frame 4A and the extending portion 3C of the gear box 3 are stretched each other in A- and B-directions shown in FIG. 14.

In this case, the first regulating surface 53c of the bending and fixing portion 53 comes into contact with the fourth regulating surface 52c of the projecting and fixing portion 52, the third regulating surface 53a of the bending and fixing portion 53 comes into contact with the sixth regulating surface 52a of the projecting and bending portion 52, and the second regulating surface 53b of the bending and fixing portion 53 comes into contact with the fifth regulating surface 52b of the projecting and fixing portion 52. Consequently, the main frame 4A is stretched in the A-direction and the extending portion 3C of the gear box 3 is stretched in the B-direction as shown in FIG. 14.

This state keeps and the operator's manual operation gradually presses a taper-shaped notch 54 made of a hard member into the space between the end surface of the extending portion 3C and the bending and fixing portion 53 by using a hammer 56, via a gad 55 from the oblique-upper direction (C-direction shown in FIG. 14) on the main frame 4A. As a result, the main frame 4A is strongly connected and is fixed to the extending portion 3C of the gear box 3 in the highly-accurately positioned state in the three x-, y-, and z-directions.

According to the sixth embodiment, the fixing state is held by using the press-in operation of the notch 54 and the pot screw 47 is screwed via the screw hole (not shown) of the bending and fixing portion 52 and via the screw hole (not shown) of the projecting and fixing portion 53. The main frame 4A may strongly be connected and fixed to the gear box 3 in the highly-accurately positioning state in the three x-, y-, and z-directions.

According to the sixth embodiment, the notch 54 may be held or may be detached.

Other structures and operations are the same as those according to the third embodiment.

Thus, according to the sixth embodiment, the same advantages as those according to the third embodiment are obtained. In addition, since the notch 54 presses the regulating surfaces, stable energization force is obtained, the positioning is accurately performed without deviation, and the connection and fixing state become strong.

(Seventh Embodiment)

Figure 15:
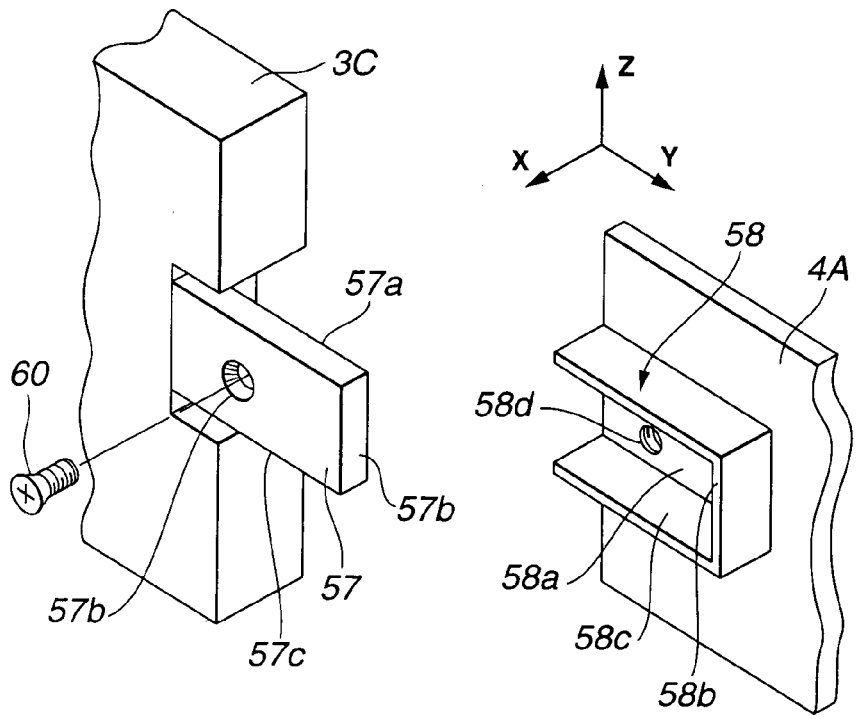
FIG. 15 is a perspective view showing an example of the structure of improved positioning and fixing means in an electric bending endoscope according to a seventh embodiment of the present invention.

FIG. 15 is a perspective view showing an example of the structure of improved positioning and fixing means in an electric bending endoscope according to a seventh embodiment of the present invention. Incidentally, the same components as those of the electric bending apparatus 2 shown according to the third embodiment are designated by the same reference numerals and are not described, and only different portions are described.

According to the seventh embodiment, referring to FIG. 15, the main frame 4A of the bending and stretch mechanism portion 4 is made of a hard member such as aluminum diecast. A bending and fixing portion 58 for fixing to the gear box 3 as positioning and fixing means is arranged to the base end portion on the gear box 3 side in the main frame 4A of the bending and stretch mechanism portion 4.

The bending and fixing portion 58 is U-shaped on the inner side surface of the base end side of the main frame 4A, and regulates three-axis directions (z-direction, y-direction, and x-direction) of the main frame 4A to the gear box 3 upon positioning to the gear box 3. The bending and fixing portion 58 further has two first regulating surfaces 58c for regulating the z-direction of the main frame 4A, a second regulating surface 58b for regulating the y-direction of the main frame 4A, a third regulating surface 58a for regulating the x-direction of the main frame 4A, and a female screw hole 58d for fixing the main frame 4A to the gear box 3.

On the other hand, the gear box 3 which is engaged with the bending and fixing portion 58 has a projecting and fixing portion 57 as the positioning and fixing means at the base end portion of an extending portion 3C extended to the main frame 4A side of the inner gear frame 10 as the hard member.

The projecting and fixing portion 57 is plate-shaped corresponding to the shape of the bending and fixing portion 58 so that it is projected in the y-direction from the base end portion of the extending portion 3C in the inner gear frame 10, and comprises a fourth regulating surface 57c which comes into contact with the first regulating surface 58c of the bending and fixing portion 58, a fifth regulating surface 57b which comes into contact with the second regulating surface 58b of the bending and fixing portion 58, a sixth regulating surface 57a which comes into contact with the third regulating surface 58a of the bending and fixing portion 58, and a plate screw hole 57d for fixing the bending and fixing portion 58.

The width and the projecting dimension of the projecting and fixing portion 57 are designed so that it is fit into the U-shaped inner portion of the bending and fixing portion 58.

In the electric bending endoscope 2 according to the seventh embodiment, referring to FIG. 15, the main frame 4A of the bending and stretch mechanism portion 4 is positioned and is fixed to the gear box 3, by fitting the bending and fixing portion 58 in the main frame 4A into the projecting and fixing portion 57 of the gear box 3.

In this case, the first regulating surface 58c of the bending and fixing portion 58 comes into contact with the fourth regulating surface 57c of the projecting and fixing portion 57, the third regulating surface 58a of the bending and fixing portion 58 comes into contact with the sixth regulating surface 57a of the projecting and fixing portion 57, and the second regulating surface 58b of the bending and fixing portion 58 comes into contact with the fifth regulating surface 57b of the projecting and fixing portion 57. Consequently, the main frame 4A is positioned to the extending portion 3C of the gear box 3 in the three directions (x-, y-, and z-directions) of the main frame 4A.

This state keeps and the main frame 4A is strongly connected and is fixed to the gear box 3 in the highly-accurately positioned state via the plate screw 57d of the projecting and fixing portion 57 and the female screw hole 58 of the bending and fixing portion 58 by using the plate screw 60.

According to the seventh embodiment, other structures and operations are the same as those according to the third embodiment.

Thus, according to the seventh embodiment, the same advantages as those according to the third embodiment are obtained. In addition, since the regulating surfaces are strongly pressed by using the plate screw 60, the positioning is accurately performed and the connection and fixing state become strong.

According to the first to seventh embodiments, a joystick, an air and water supply button, a suction button, and switches such as a video switch may be connected and be fixed to the inner gear frame as the hard member in the gear box 3, in addition to the main frame 4A in the bending and stretch mechanism portion 4 connected to the inserting portion 6 and the universal cord connected to the bending and stretch control device.

According to the third and seventh embodiments, the description is given of the case of the positioning and strong connection and fixing between the main frame 4A and the gear box 3 by using the bending and fixing portion and the projecting and fixing portion as the positioning and fixing means. However, the connecting and fixing member 8 (refer to FIG. 1) used for the first and second embodiments may be used together and, in this case, further stronger connection and fixing is accomplished. Alternatively, the main frame 4A may be connected and be fixed to the gear box 3 by using only the positioning and fixing means comprising the bending and fixing portion and the projecting and fixing portion without using the connecting and fixing member 8. In this case, the connecting and fixing member 8 is deleted and this contributes to the small size of the gear box 3.

The present invention is not limited to the third to seventh embodiments. The present invention can be applied to the case of positioning the three (x-, y-, and z-directions) of the main frame 4A to the gear box 3 by using a plurality of regulating surfaces and to the case of using the positioning and fixing means by which the fixing is performed by the screw operation. Further, the present invention can be applied to the combination of the third to seventh embodiments and to the modification thereof.

In the electric bending endoscope 2 of the present invention, the bending operability is improved. Technologies for improvement of the bending operability in the electric bending endoscope 2 of the present invention are disclosed here.

Figure 16:
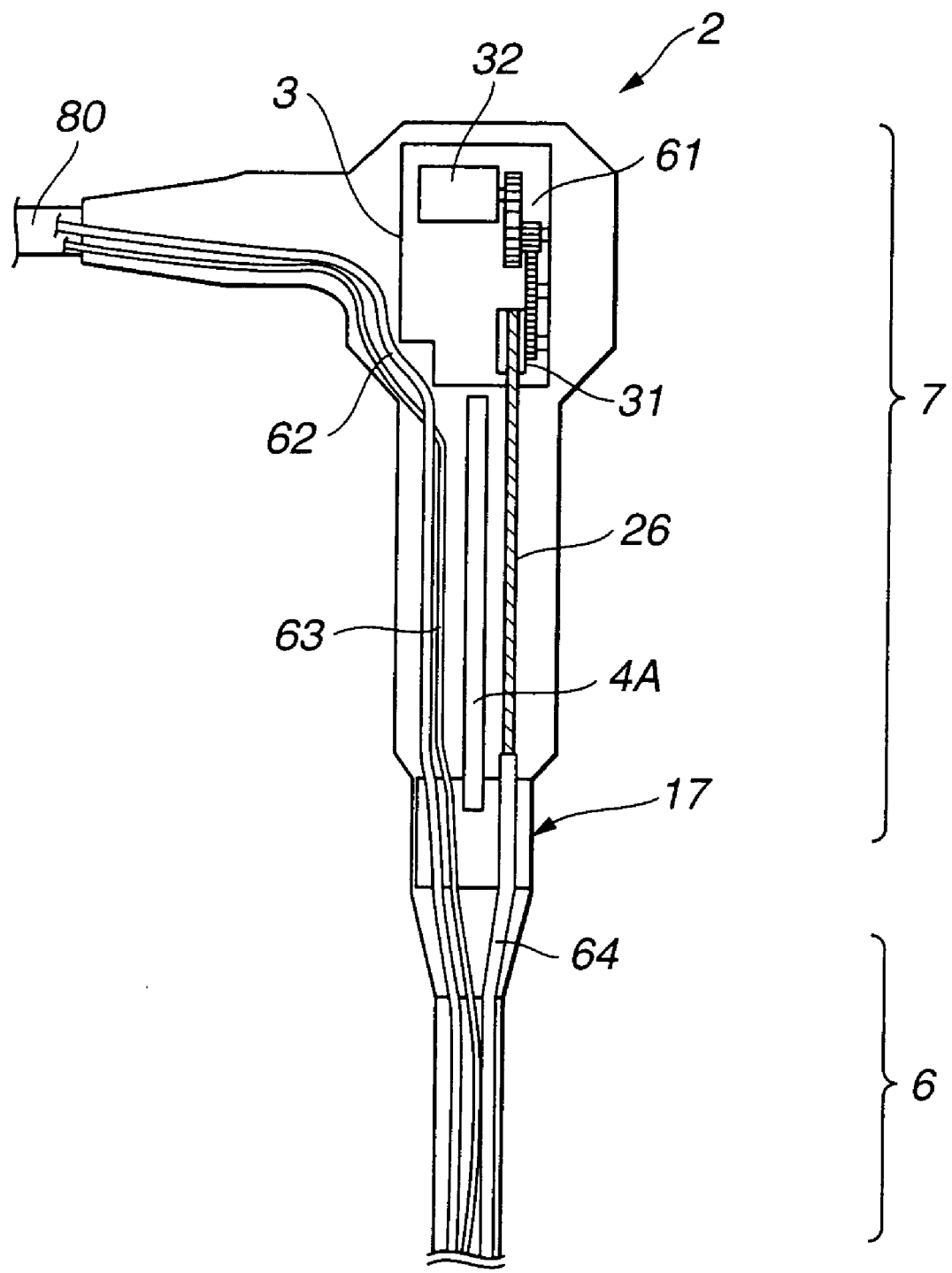
FIG. 16 is a diagram showing the layout of accommodating members in an operating portion provided for the electric bending endoscope of the present invention.

FIGS. 16 and 17 shows diagrams for explaining the improvements of the bending operability in the electric bending endoscope of the present invention. FIG. 16 is a diagram showing the layout of accommodating members in an operating portion provided for the electric bending endoscope according to the present invention. FIG. 17 is a cross-sectional view showing the layout of a bending and stretch mechanism and switches in the operating portion provided for the electric bending endoscope according to the present invention. Incidentally, the same components shown in FIGS. 16 and 17 as those of the electric bending apparatus shown according to the first embodiment are designated by the same reference numerals and are not described, and only different portions are described.

Referring to FIG. 16, in the electric bending endoscope 2 of the present invention, the operating portion 7 comprises sliding members for the bending operation, namely, the chain 26A of the bending and stretch mechanism portion 4 and the bending operation wire 26, the signal cable 24 for transmitting the image pick-up signal from the image pick-up device 24 (refer to FIG. 4) such as the CCD, and connecting cables such as the light guide 62 for transmitting the illumination light so that they are detached via the main frame 4A of the bending and stretch mechanism portion 4 connected and fixed to the gear box 3.

The base end portion of the main frame 4A is arranged throughout the connecting tube 17. The chain 26A is inserted in a protecting coil 64 which is extended to the overlapped position of the base end portion of the main frame 4A in the operating portion 7 via the connecting tube 17 from the inserting portion 6.

With the above structure, in the operating portion 7, the interposition of the main frame 4A prevents the contact state of the chain 26A and the bending operation wire 26 in the bending and stretch mechanism portion 4 as the sliding member, the light guide 62, and the signal cable 63. Thus, various operations such as the bending operation in the electric bending endoscope are certainly executed without the hang-up of the chain 26A due to the contact state of the members and without the short circuit of the signal cables. In the range from the base end portion of the main frame 4A to the inserting portion 6, the protecting coil 64 for covering the bending operation wire 26 is extended from the connecting tube 17. As a result, it is possible to prevent the contact state of the light guide 62 and the signal cables.

Referring to FIG. 17, in the electric bending endoscope 2 of the present invention, the center axis of the sprocket 31 of the bending and stretch mechanism portion 4 contact with the gear box 3 (not shown) is arranged to the front side of the operating portion 7 to which the various switches (the air and water supply button 66 and the suction button 67) are arranged, with respect to the center axis of the inserting portion 6. On the grip portion 7a in the operating portion 7, arranged to the chain 26A engaged with the sprocket 31 in the contact state, opposed thereto, are a pair of cylindrical members 65 having the slidability for bending the chain 26A along the center axis of the inserting portion 6. Thus, the center axis of the sprocket 31 is arranged to the front side of the operating portion 7, with respect to the center axis of the inserting portion 6. Therefore, a contact portion of a thumb base of the grip portion 7a in the operating portion 7 becomes a sloped surface as shown in FIG. 17, and the grip portion 7a is easily gripped.

Further, in the electric bending endoscope 2 shown in FIG. 17, an angle θ1 is formed between the center axis of the inserting portion 6 and the center axis of the joystick 70a as the bending operation input means 70 at the neutral position thereof, and is (135°±15°). An inclined angle θ2 of the joystick 70a is ±30° from the center of the joystick 70a. The inclined center position of the joystick 70a is arranged in front of the operating portion 7 with respect to the center axis of the inserting portion 6. Thus, upon gripping the grip portion 7a substantially in the vertical state by the four fingers except for the thumb of the operator, the thumb operating the joystick 70a is naturally placed to the position contact to the joystick 70a. Since the inclined angle θ2 is ±30° from the center of the joystick 70a, it is possible to prevent the deviation of the top position of the joystick 70a out of a thumb-operable range.

Further, in the electric bending endoscope 2 shown in FIG. 17, an angle θ3 is formed between the center axis of the joystick 70a at the neutral position thereof and the operation direction of the operation switches including at least the air and solution button 66 and the suction button 67. The angle θ3 is 30° or more.

When the angle θ3 is not more than 30° where the angle θ3 is formed between the center axis of the joystick 70a operated by the thumb at the neutral position thereof and the operation direction of the operation switches by the index finger or middle finger, the force is applied to the index finger and the middle finger upon operating the joystick 70a by the thumb. The opposed operation switches (the air and water supply button 66 and the suction button 67) are pressed irrespectively of the operator's desire. Alternatively, upon operating the operation switches by the middle finger or the index finger, the joystick 70a might be pressed though he does not desire it. However, in the example, as mentioned above, the angle θ3 of 30° or more is formed between the center axis of the joystick 70a at the neutral position thereof and the operation direction of the operation switch including at least the air and solution button 66 and the suction button 67. Thus, both upon operating the joystick 70a by the thumb and upon operating the operation switches by the middle finger or the index finger, the above operation results in reducing the danger for operating the operation switches (the air and water supply button 66 and the suction button 67) arranged to the opposed surface of the operating portion or the joystick 70a though he does not desire this.

The above technologies improve the operability of the electric bending endoscope 2.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An electric bending endoscope comprising:
   an inserting portion having a bending portion which is inserted in a subject;
   an operation wire which is inserted in the inserting portion for bending the bending portion;
   a motor for supplying a driving force to the operation wire for bending the bending portion;
   a first unit for holding the motor;
   a driving force transmitting member which transmits the driving force supplied from the motor to the operation wire in order to bend the bending portion, the driving force transmitting member being connected to the operation wire via a connecting portion;
   a second unit for holding the driving force transmitting member;
   a first connecting member for connecting the first unit and the second unit so that the driving force of the motor maybe transmitted to the driving force transmitting member; and
   a second connecting member for connecting the second unit and the inserting portion so that the bending portion many be bent by the driving force transmitted from the driving force transmitting member.

2. An electric bending endoscope according to claim 1, wherein the driving force transmitting member is rotatably supported by the second unit in order to operate a bending operation member passed through the inserting portion in accordance with the driving of the motor, the first unit has an attaching hole which accommodates a rotating shaft of the driving force transmitting member and at least three positioning holes arranged near the attaching hole, and the first connecting member has a hole through which the rotating shaft is passed, a projecting and positioning piece which is accommodated in the attaching hole, and at least three projecting and positioning pins which are fit into the positioning holes.

3. An electric bending endoscope according to claim 2, wherein the first unit is further provided with an opening which connectably accommodates the second unit to the motor and the driving force transmitting member, and a guide hole which guides and accommodates the rotating shaft upon mounting the second unit via the opening.

4. An electric bending endoscope according to claim 1, wherein the second connecting member holds a universal cord for connecting the electric bending endoscope to a peripheral device, wherein the first unit comprises an outer frame and an inner frame for holding the motor, and the second connecting member is connected to the inner frame and the inner frame is accommodated in the outer frame so as to be at least partially exposed to form an exposed portion, and the second connecting member is fixed to the exposed portion.

5. An electric bending endoscope according to claim 4, wherein the second connecting member has a ring-shaped holding portion for holding the universal cord and a fixing portion for fixing the holding portion to the inner frame at at least three positions.

6. An electric bending endoscope according to claim 5, wherein the holding portion has a plurality of screw holes on a peripheral surface and the universal cord is fit by screw operation of a screw via a screw hole arranged to a connector at an edge portion of the universal cord and the screw holes of the holding portion.

7. An electric bending endoscope according to claim 4, further comprising:
   a fixing member which fixes the inner frame to a main frame in the second unit.

8. An electric bending endoscope according to claim 7, wherein the main frame is positioned to the inner frame by using a positioning tool for positioning the main frame in the second unit in three-axis directions to the inner frame, and the inner frame and the main frame in the second unit are fixed by using a fixing member for fixing them.

9. An electric bending endoscope according to claim 8, wherein a positioning and fixing member for positioning and fixing the main frame in the second unit in three-axis directions to the inner frame is arranged to a connecting portion of the inner frame and the main frame.

10. An electric bending endoscope according to claim 7, wherein the bending operation member is constituted such as to slide with respect to the second unit in accordance with the driving of the motor when bending the bending portion, and the main frame in the second unit is arranged so that a signal cable which is passed through the endoscope for transmitting an endoscope image pick-up signal, a light guide for transmitting illumination light, and the bending operation member are detached.

11. An electric bending endoscope according to claim 1, wherein the first unit comprises an inner frame for holding the motor and an outer frame for accommodating the inner frame, the inner frame having a holding member for holding a universal cord for connecting the electric bending endoscope to a peripheral device.

12. An electric bending endoscope comprising:

an inserting portion which is inserted in a subject;

bending means for bending the inserting portion;

driving force supplying means for supplying a driving force for bending the inserting portion;

driving force transmitting means which transmits the driving force supplied from the driving force supplying means to the inserting portion in order to bend the inserting portion;

first connecting means for connecting the driving force supplying means and the driving force transmitting means in order to transmit the driving force supplied from the driving force supplying means to the driving force transmitting means; and second connecting means for connecting the driving force transmitting means and the inserting portion in order to transmit the driving force transmitted to the driving force transmitting means to the bending portion.

* * * * *